United States Patent [19]

Elhammer

[11] Patent Number: 5,861,318

[45] Date of Patent: Jan. 19, 1999

[54] SCINTILLATION PROXIMITY ASSAY FOR N-ACETYLGALACTOSAMINYLTRANSFERASE ACTIVITY

[75] Inventor: Ake P. Elhammer, Kalamazoo, Mich.

[73] Assignee: Pharmacia & Upjohn Company, Kalamazoo, Mich.

[21] Appl. No.: 340,283

[22] Filed: Nov. 16, 1994

[51] Int. Cl.$^6$ .................................................. G01N 33/543
[52] U.S. Cl. .......................... 436/523; 436/524; 436/528; 435/15
[58] Field of Search .................................... 436/523, 524, 436/528; 435/15

[56] References Cited

U.S. PATENT DOCUMENTS 4,568,649  2/1986  Bertoglio-Matte ....................... 436/534

FOREIGN PATENT DOCUMENTS 0 397 875 A3  9/1990  European Pat. Off. .
0 656 422 A1  6/1995  European Pat. Off. .
WO 94/26906  11/1994  WIPO .

OTHER PUBLICATIONS

Elhammer, Å.P., Poorman, R.A., Brown, E., Maggiora, L.L., Hoogerheide, J.G., and Kezdy, F.J. (1993) *J. Biol. Chem.* 268, 10029–10038.

Homa, F.L., Hollander, T., Lehman, D.J., Thomsen, D., and Elhammer, Å.P. (1993) *J. Biol. Chem.* 268, 12609–12616.

Homa, F.L., Baker, C.A., Thomsen, D.R., and Elhammer, Å.P. (1994) *Prot. Expr. Purif.* in press.

O'Connel, B.C., Hagen F.K., and Tabak, L.A. (1992) *J. Biol. Chem.* 267, 25010–25018.

Wang, Y., Agrawal, N., Eckhardt, A.E., Stevens, R.D., and Hill, R.L. (1993) *J. Biol. Chem.* 268, 22979–22983.

Young, J.D., Tsuchiya, D., Sandlin, D.E., and Holroyde, M.J. (1979) *Biochem.* 18, 4444–4448.

Hagopian, A., and Eylar, E.H. (1968) *Arch. Biochem. Biophys.* 128, 422–433.

Hagopian, A., Westall, F.C., Whitehead, J.S., and Eylar, E.H. (1971) *J. Biol. Chem.* 246, 2519–2523.

Sadler, J.E. (1984) in *Biology of Carbohydrates* (Ginsburg, V., & Robbins, P.W., Eds.) 2, 199 288, John Wiley & Sons, New York.

Schachter, H., and Brockhausen, I. (1992) in *Glycoconjugates* (Allen, H.J., & Kisailu, E.C., Eds.) pp. 263–232, Marcel Dekker, Inc., New York.

*Primary Examiner*—Sheela Hupp
*Attorney, Agent, or Firm*—Thomas A. Wootton

[57] ABSTRACT

This invention comprises a scintillation proximity assay designed to assay for the presence of N-acetylgalactosaminyltransferase, also known as GalNAc-transferase. The assay is most conveniently carried out on 96-well microtiterplates. The assay is especially suitable for large volume screens for compounds affecting GalNAc-transferase activity.

14 Claims, 5 Drawing Sheets

SCINTILLATION PROXIMITY ASSAY FOR N-ACETYLGALACTOSAMINYLTRANSFERASE ACTIVITY

FIELD OF THE INVENTION

This invention relates to the field of scintillation proximity assays designed to assay for the presence of UDP-GalNAc:polypeptide, N-acetylgalactosaminyltransferase, also known as GalNAc-transferase.

INFORMATION DISCLOSURE

Elhammer, Å. P., Poorman, R. A., Brown, E., Maggiora, L. L., Hoogerheide, J. G., and Kezdy, F. J. (1993) *J. Biol. Chem.* 268, 10029–10038. Elucidation of the acceptor requirements of the enzyme and construction of acceptor peptides.

Homa, F. L., Hollander, T., Lehman, D. J., Thomsen, D., and Elhammer, Å. P. (1993) *J. Biol. Chem.* 268, 12609–12616. Describes the cloning of GalNAc-transferase, the enzyme used in the assay.

Homa, F. L., Baker, C. A., Thomsen, D. R., and Elhammer, Å. P. (1994) *Prot. Expr. Purif.* in press. Describes conversion of the full-length, cloned molecule to a soluble enzyme and expression and purification of the (soluble) molecule.

J. H. Bertoglio-Matte, U.S. Pat. No. 4,568,649, issued Feb. 4, 1986, "Immediate Ligand Detection Assay" Describes a SPA based assay for detecting the presence of minute amounts of an organic reactant in a test sample.

O'Connel, B. C., Hagen F. K, and Tabak, L. A. (1992) *J. Biol. Chem.* 267, 25010–25018. The acceptor specificity of GalNAc-transferase using synthetic peptides is discussed.

Wang, Y., Agrawal, N., Eckhardt, A. E., Stevens, R. D., and Hill, R. L. (1993) *J. Biol. Chem.* 268, 22979–22983. Discusses the acceptor specificity of GalNAc-transferase using synthetic peptides.

Young, J. D., Tsuchiya, D., Sandlin, D. E., and Holroyde, M. J. (1979) *Biochem.* 18, 4444–4448. The original article discussing acceptor specificity of GalNAc-transferase using synthetic peptides.

Hagopian, A., and Eylar, E. H. (1968) *Arch. Biochem. Biophys.* 128, 422–433. Background information on the use of synthetic (in this case a modified mucin) acceptors for the assay of GalNAc-transferase activity.

Hagopian, A., Westall, F. C., Whitehead, J. S., and Eylar, E. H. (1971) *J. Biol. Chem.* 246, 2519–2523. Background information on the use of synthetic (in this case a modified mucin) acceptors for the assay of GalNAc-transferase activity.

Sadler, J. E. (1984) in *Biology of Carbohydrates* (Ginsburg, V., & Robbins, P. W., Eds.) 2, 199–213, John Wiley & Sons, New York. Comprehensive review of O-linked glycosylation.

Schachter, H., and Brockhausen, I. (1992) in *Glycoconjugates* (Allen, H. J., & Kisailu, E. C., Eds.) pp. 263–232, Marcel Dekker, Inc., New York. Comprehensive review of O-linked glycosylation.

BACKGROUND

Mucin type O-glycosidically linked oligosaccharides have been described on a wide variety of protein molecules (Sadler, 1984). These structures constitute essential components in an equally wide variety of biological functions (e.g., Paulson, 1989; Jentoft, 1990 and references therein). The initial reaction in the biosynthesis of O-linked oligosaccharides is the transfer of N-acetylgalactosamine from the nucleotide sugar, UDP-N-acetylgalactosmine, to a serine or threonine residue on the acceptor polypeptide. This reaction, which can occur post-translationally, is catalyzed by a GalNAc-transferase enzyme (GalNAcT) called, UDP-GalNAc:polypeptide,N-acetylgalactosaminyltransferase. This is an intracellular membrane bound enzyme believed to be localized in the secretory pathway.

The exact location(s) of GalNAc-transferases in in vivo systems is not precisely known. It has been reported that the initial addition of N-acetylgalactosamine to the acceptor protein can take place early (even co-translationally) in the rough endoplasmic reticulum (ER). Other authors have suggested that this reaction is a post-translational event occurring in later ER compartments and/or in the cis region of the Golgi complex (e.g. Hanover et al. (1982) *J. Biol. Chem.* 257:10172–10177; Roth (1984) *J. Cell Biol.* 98:399–406; Elhammer and Kornfeld (1984) *J. Cell Biol.* 98:327–331; Tooze et al. (1988) *J. Cell Biol.* 106:1475–1487; Deschuyteneer et al. (1988) *J. Biol. Chem.* 263:2452–2459; Ulmer and Palade (1989) *Proc. Natl. Acad. Sci. (U.S.A.)* 89:663–667; Wertz et al. (1989) *J. Virol.* 63:4767–4776; Piller et al. (1989) *Eur. J. Biochem.* 183:123–135; Piller et al. (1990) *J. Biol. Chem.* 265:9264–9271.

Evidence has also been presented for a model in which transfer of N-acetylgalactosamine to Ser/Thr may occur in several compartments in the secretory pathway, including compartments later than the Golgi complex (Schachter and Brockhausen (1992) in *Glycoconjugates,* Allen and Kisailus, eds., pp. 263–332, Marcel Dekker Inc., New York). Elongation and termination of O-linked oligosaccharides is accomplished by sequential addition of individual monosaccharides by specific transferases (Roseman (1970) *Chem. Phys. Lipids* 5:270–280); current data suggest that these reactions are localized primarily in the Golgi apparatus (Schachter and Brockhausen, supra).

Enzyme-mediated synthesis of O-glycosidically linked oligosaccharides offer significant advantages over the classical synthetic organic pathways, producing very high yields of carbohydrates (e.g., oligosaccharides and/or polysaccharides), under mild conditions in aqueous solutions, and without generating notable amounts of undesired side products. However, an absolute prerequisite for this type of synthesis is the availability of cloned glycosyltransferases.

Endogenous enzymes can be isolated from most eucaryotic sources; however, these proteins are only found in low concentrations, so this is generally a difficult, time consuming procedure, yielding amounts of purified enzymes which are insufficient for in vitro synthesis work. Another complication is that the endogenous enzymes invariably are membrane bound, this complicates purification and in vitro uses of the enzyme. A cloned enzyme, on the other hand, can usually be expressed as a soluble enzyme with comparative ease.

In light of the considerable value of carbohydrates, there is accordingly a strong felt need for fast and quick assays of GalNAc-transferase.

Assays for GalNAc-transferase activity typically involve incubation of the activity containing preparation with radioactively labeled UDP-GalNAc and either an intact acceptor protein (e.g., basic myelin protein), a fragment(s) of a deglycosylated protein (e.g., various apomucins) or a synthetic peptide (e.g., Hagopian et al., 1971; Hagopian and Eylar, 1968; Young et al., 1979; Wang et al., 1992; Elhammer et al., 1993). The acceptor (sequence) requirements of the enzyme have recently been elucidated to a considerable extent and synthesis of efficient acceptor peptides can be accomplished quite readily (O'Connel et al., 1992; Wang et al., 1993; Elhammer et al., 1993). Following transfer of the radioactive sugar to the polypeptide acceptor, the product is isolated and the amount of enzymatic transfer quantitated by measuring the amount of radioactivity incorporated into the acceptor. Thus, in principle, assays for GalNAc-transferase activity are comparatively straight-forward.

A considerable technical problem associated with these assays, however, is the isolation of the glycosylated reaction product. For peptide acceptors, methods employed to date include chromatography on ion-exchange, size exclusion or reverse phase columns and, for protein acceptors, various (e.g., TCA) precipitation procedures. In the former case, a number of chromatography columns have to be prepared, equilibrated and developed for each experiment, in the latter, extensive washing procedures have to be carried out in order to reduce background radioactivity. Hence, typical GalNAc-transferase assays (using either acceptor) are both labor intense and time-consuming.

Here we describe a novel approach for the quantitation of the reaction products in GalNAc-transferase assays that employs fewer steps, takes less time, and is much more suitable than other assays currently available for screening for GalNAc-transferase.

SUMMARY OF THE INVENTION

The invention comprises a Scintillation Proximity Assay (SPA) for the detection of GalNAc-transferase activity. Embodiments of the assay include: Scintillation Proximity Assay (SPA) beads for the quantitation of incorporated radioactivity; an appropriate receptor interacting with an appropriate ligand produced as a result of reaction with the enzyme, GalNAc-transferase; an appropriate receptor that is a lectin coated SPA bead and the ligand is an acceptor peptide that is not conjugated; a lectin taken from the group consisting of Salvia Sclarea, Helix Pomatia, or Vicia Villosa; an appropriate receptor that is an antibody coated SPA bead and the ligand is a acceptor peptide that is not conjugated; an antibody that recognizes the Tn antigen; an appropriate receptor that is an antibody coated SPA bead and the ligand is a modified acceptor peptide fused to an antigenic peptide sequence; an antigenic peptide sequence that is either a portion of MYC (e.g. AEEQKLISEEDLLRKRREQLKHKLEQLRNSC( SEQ. ID. NO.1)) or FLAG (DYKDDDK SEQ. ID. NO.2)); an appropriate receptor that is a avidin or streptavidin coated SPA bead and the ligand is a biotin conjugated acceptor peptide; a biotin conjugated acceptor peptide having a peptide sequence of at least 3 amino acids where one of the three amino acids is an acceptor peptide that is Ser or Thr; a biotin conjugated acceptor peptide and the peptide sequence may be described as having the amino acids $R_{-1}$ to $R_{11}$, as shown,

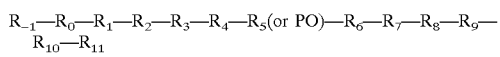

$R_5$ (or PO) is the acceptor amino acid and is Ser or Thr;
$R_4$ and $R_6$ are independent and are Asp, Asn, Glu, Gln, Ser, Gly, His, Arg, Thr, Ala, Pro, Tyr, Val, Met, Ile, Leu, Phe, Lys, Cys, or Trp;

and $R_{-1}-R_3$ and $R_7-R_{11}$ are independent and are, no amino acids, or any of the following amino acids, Asp, Asn, Glu, Gln, Ser, Gly, His, Arg, Thr, Ala, Pro, Tyr, Val, Met, Ile, Leu, Phe, Lys, Cys, or Trp; a biotin conjugated acceptor peptide and the peptide sequence may be described as having the amino acids $R_1$ to $R_9$, as shown,

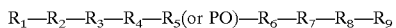

$R_5$ (or PO) is the acceptor amino acid and is Ser or Thr;
$R_4$ and $R_6$ are independent and are Asp, Asn, Glu, Gln, Ser, Gly, His, Arg, Thr, Ala, Pro, Tyr, Val, Met, Ile, Leu, Phe, Lys, Cys, or Trp;
and $R_1-R_3$ and $R_7-R_9$ are independent and are, no amino acids, or any of the following amino acids, Asp, Asn, Glu, Gln, Ser, Gly, His, Arg, Thr, Ala, Pro, Tyr, Val, Met, Ile, Leu, Phe, Lys, Cys, or Trp; the peptide sequence where the peptides are any of the sequences shown in CHART 1; where the amino acids $R_1$ to $R_9$, in the acceptor peptide, are any of the following amino acids: Asp, Asn, Glu, Gln, Ser, Gly, His, Arg, Thr, Ala, Pro, Tyr, Val, Met, Ile, Leu, Phe, Lys, Cys, or Trp; where the amino acids $R_1$ to $R_9$ are any of the following amino acids: Ser, Thr, Pro, Ala, or Gly; or where the peptide sequences are any of the following, RTPPP (SEQ. ID. NO.3), RSPPP (SEQ. ID. NO.4), PPASTSAPG (SEQ. ID. NO.5), or PPASSSAPG (SEQ. ID. NO.6).

Figure 1:
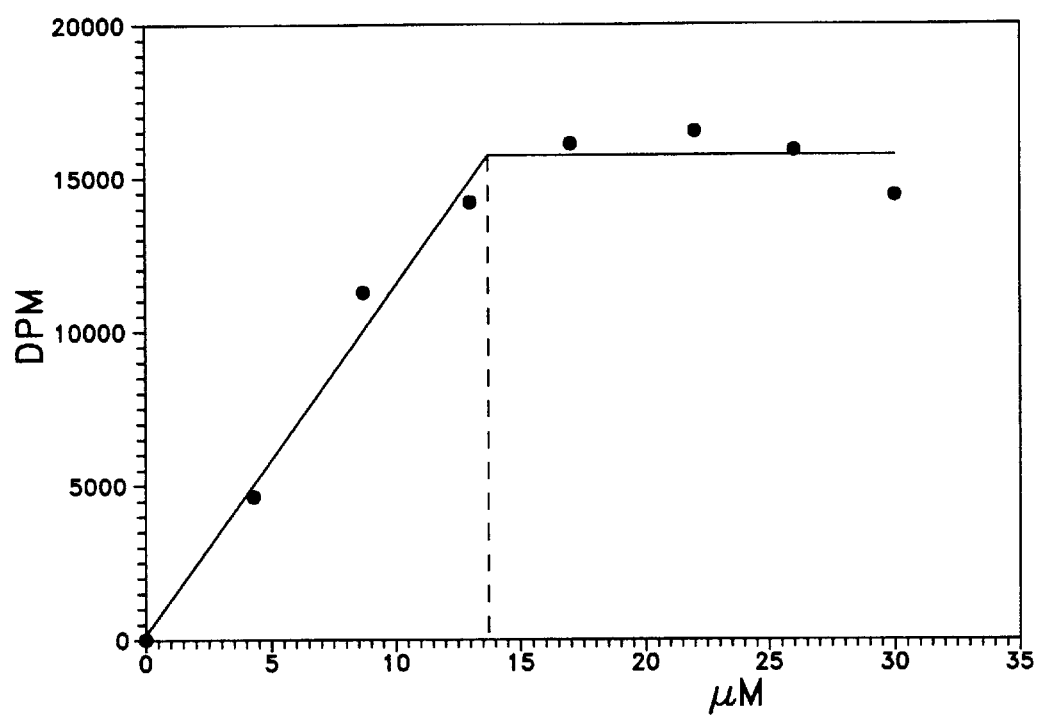
FIG. 1. Effect of acceptor conjugate concentration on the formation of reaction product.

ADDITIONAL DESCRIPTION OF THE INVENTION AND DESCRIPTION OF THE PREFERRED EMBODIMENTS

Definitions and Materials

SPA is Scintillation Proximity Assay. Refer to U.S. Pat. No. 4,568,649 issued 4 Feb. 1986, for a complete description of a SPA system. U.S. Pat. No. 4,568,649 incorporated by reference. GalNAc-transferase is UDP-GalNAc: polypeptide:N-acetylgalactosaminyltransferase.

(M+H)+ is the mass of the ion detected by the MS; this equals the mass of the molecule (M) plus the mass of one proton (H) and the proton also adds one positive charge (+).

$K_m$ is the so called Michaelis-Menten constant. The numerical value of the constant provides the substrate concentration at half maximal reaction velocity ($V_{max}/2$).

DPM or dpm is disintegrations per minute. H, h or hr is hour. HPLC is high performance (or pressure) liquid chromatography. TFA is Trifluoro Acetic Acid. The abbreviation "mU" (milli Units) is a measure of enzyme activity; one U equals 1 nmole GalNAc transferred per minute.

Amino acid residues referred to herein are listed below, they may also be given either three letter or single letter abbreviations, as follows:

Alanine, Ala, A; Arginine, Arg, R; Asparagine, Asn, N; Aspartic acid, Asp, D; Cystein, Cys, C; Glutamine, Gln, Q; Glutamic Acid, Glu, E; Glycine, Gly, G; Histidine, His, H; Isoleucine, Ile, I; Leucine, Leu, L; Lysine, Lys, K;

Methionine, Met, M; Phenylalanine, Phe, F; Proline, Pro, P; Serine, Ser, S; Threonine, Thr, T; Tryptophan, Trp, W; Tyrosine, Tyr, Y; Valine, Val, V; Aspartic acid or Asparagine, Asx, B; Glutamic acid or Glutamine, Glx, Z; Any amino acid, Xaa, X.

All amino acids have a carboxyl group and an amino group. The amino group of the amino acid is also referred to as the "N-terminus" of the amino acid. The carboxyl group of an amino acid is also referred to as the "C-terminus" of the amino acid. The "N-terminus" of an amino acid may form a peptide bond with a carboxyl group of another compound. The carboxyl group that combines with the "N-terminus" of an amino acid may be the carboxyl group of another amino acid or it may be from another source. If several amino acids are linked into a polypeptide, then the polypeptide will have a "free" (unconjugated) N-terminus and a "free" C-terminus.

Peptide Sequences. PPASTSAPG is Pro-Pro-Ala-Ser-Thr-Ser-Ala-Pro-Gly (SEQ. ID. NO.5); PPASSSAPG is Pro-Pro-Ala-Ser-Ser-Ser-Ala-Pro-Gly (SEQ. ID. NO.6); RTPPP is Arg-Thr-Pro-Pro-Pro (SEQ. ID. NO.3); RSPPP is Arg-Ser-Pro-Pro-Pro (SEQ. ID. NO.4).

For the purposes of this invention, "acceptor" can be any peptide sequence, either free or conjugated, either independent or connected to another compound, that accepts the UDP-GalNAc enzyme.

The words "acceptor peptide" refers to a peptide sequence, such as PPASTSAPG (SEQ. ID. NO.5), or to the sequences disclosed in Elhammer, Å. P., Poorman, R. A., Brown, E., Maggiora, L. L., Hoogerheide, J. G., and Kezdy, F. J. (1993) *J. Biol. Chem.* 268, 10029–10038, incorporated by reference herein, or to any peptide sequence that accepts the UDP-GalNAc transferase enzyme.

The words "acceptor-conjugate" refers to either an acceptor peptide by itself, in the role of a acceptor-conjugate, or more commonly, it refers to an acceptor peptide, such as PPASTSAPG (SEQ. ID. NO.5), that is conjugated to a molecule, such as biotin, that has a high affinity for a compound attached to, or part of, the SPA beads, such as avidin or streptavidin. See, U.S. Pat. No. 4,568,649 for a more complete description of possible acceptor-conjugates. The words "acceptor-biotin-conjugate" would refer to an acceptor-conjugate where biotin was conjugated with the acceptor peptide. The words, "acceptor-biotin-alanine-conjugate" refers to the acceptor peptide conjugated to biotin via alanine, one example of which is biotin-βAβAβA-PPASTSAPG (SEQ. ID. NO.8). The alanine acts as a spacer to move the peptide a suitable distance from the biotin. The spacer is not essential but it seems to improve reactivity. Any suitable spacer should have similar effects.

Starting Materials

UDP-N-[1-$^3$H]-acetylgalactosamine (8.3 Ci/mmol) and SPA beads may be purchased from Amersham Corp. of Amersham Place, Little Chalfont, England. UDP-N-acetylgalactosamine may be purchased from Sigma Chemical Corp. One cc Bond Elut $C_{18}$ columns may be purchased from Varian. White Microfluor microtiter plates with round bottom wells may be purchased from Dynatech Laboratories. Purified recombinant, soluble GalNAc-transferase may be prepared as described by Homa et al. (1994) Prot. Expr. Purif in press., incorporated by reference.

All other reagents are obtainable from standard sources. The sources provided in the descriptions below represent just one possible source among many that would be known to one skilled in the art.

Solid phase peptide synthesis (Barany & Merrifield, 1979) is performed at 0.5 mmole scale utilizing $OCH_2$ Pam resin, available from Applied Biosystems Inc., Foster City, Calif., on an Applied Biosystems Inc. 430A Peptide Synthesizer.

Beta-Alanine may be obtained from Advanced Chemtech, Louisville, Ky. Other amino acids may be obtained from Applied Biosystems Inc.

Biotin in the form of N-hydroxysuccinimide-biotin is available from Pierce Chemical Co.

Utility of the Invention

This invention provides a method to assay GalNAc-transferase activity. The assay is conveniently carried out on 96-well microtiterplates. The assay is suitable for large volume screens for compounds affecting GalNAc-transferase activity. The assay may be made and used as a kit.

Detailed Description of the Invention

This invention comprises an acceptor or conjugated-acceptor, SPA beads and quantitation of incorporated radioactivity. One embodiment comprises a biotinylated acceptor peptide, streptavidin coated SPA beads and quantitation of incorporated radioactivity on a microplate scintillation counter. The assay is ideally suited for experiments involving large series screens for compounds affecting the activity of UDP-GalNAc:polypeptide, N-acetylgalactosaminyltransferase (GalNAc-transferase).

The assay described herein provides a fast, simple and reproducible way of measuring GalNAc-transferase activity. Large numbers of samples can easily be processed and, using the recombinant enzyme, excellent signal-to-noise ratios are easily obtained. The availability of this assay should greatly facilitate screenings for specific GalNAc-transferase inhibitors.

Several embodiments of this invention are described: There are four different, but related, versions of this invention. These different versions are lettered A through D. All the versions utilize SPA beads having appropriate receptors that interact with ligands produced as a result of a reaction with the enzyme, GalNAc-transferase.

Version A involves the use of an acceptor peptide, that is not conjugated, and isolation and quantitation of the reaction product, on lectin coated SPA beads. Following GalNAc-transferase catalyzed transfer of $^3$H-GalNAc from UDP-$^3$H-GalNAc to the acceptor, the glycosylated product is adsorbed to SPA beads coated with a GalNAc-specific lectin. This will bring the radioactive sugar on the reaction product in close enough proximity to the scintillant in the SPA beads to elicit a signal which can be quantitated in a scintillation detection device. Examples of lectins which specifically binds GalNAc and which could be used for this type of assay are: Salvia Sclarea, Helix Pomatia and Vicia Villosa. Since it is likely that the lectins used for isolation of the reaction product also will have some affinity for the radioactive nucleotide sugar in the assay, this type of assay will probably be applicable primarily to assays using multi-site acceptors.

Version B involves the use of an unconjugated acceptor peptide and isolation and quantitation of the reaction product by antibody coated SPA beads. Following GalNAc-transferase catalyzed transfer of $^3$H-GalNAc from UDP-$^3$H-GalNAc to the acceptor, the glycosylated product is adsorbed to SPA beads coated with a GalNAc-specific antibody. GalNAc conjugated by an O-glycosidic linkage to a peptide segment is a well documented cancer antigen, the so called Tn antigen, in humans; antibodies specifically recognizing this structure are commercially available.

Detection and quantitation of the product generated in this type of assay follows the same principle as in version A.

Version C involves the use of a modified acceptor peptide in which the GalNAc-transferase acceptor sequence is fused to an antigenic peptide sequence. Several such (antigenic) sequences and their corresponding antibodies are described in the literature and some of them, e.g. portions of MYC (e.g. AEEQKLISEEDLLRKRREQLKHKLEQLRNSC (SEQ. ID. NO.1)) and FLAG (DYKDDDK (SEQ. ID. NO.2)), are commercially available. Thus, in this type of assay the reaction product is adsorbed on SPA beads coated with an antibody which specifically recognizes the antigenic sequence fused to the acceptor. Detection and quantitation of the product generated in this type of assay follows the same principle as in version A.

Version D involves the use of biotin conjugated acceptor peptides and avidin or streptavidin coated SPA beads. Specific examples and experimental details of this embodiment are provided below.

In one embodiment of a Version D type invention, a previously described (Elhammer et al. (1993) *J. Biol. Chem.*, 268, 10029–10038) acceptor peptide, PPASTSAPG (SEQ. ID. NO.5), is conjugated to biotin via three β-alanine residues. This makes an acceptor-conjugate, which, in conventional assays, has a $K_m$ comparable to that of the unconjugated peptide and which can be adsorbed to avidin or streptavidin. Activity assays using this peptide in combination with ³H-labeled UDP-GalNAc (donor substrate) and avidin coated SPA beads result in levels of incorporated radioactivity 10 times greater than background.

An analysis of the time dependency of the enzymatic reaction (using the biotinylated acceptor peptide) yields a $K_m$ of 0.38±0.12 μM for UDP-GalNAc. Using, for example, 4 mg of SPA beads, an acceptor concentration of 17 μM, a nucleotide sugar concentration of approximately 0.5 μM and an enzyme concentration of approximately 7.5 U/ml, the assay demonstrates an approximately linear formation of product for at least 60 minutes.

The assay is most conveniently carried out on 96-well microtiterplates. It is especially suitable for large volume screens for compounds affecting GalNAc-transferase activity.

Synthesis of the Biotinylated Acceptor Peptide.

Solid phase peptide synthesis (Barany & Merrifield, 1979) is performed at 0.5 mmole scale utilizing OCH₂ Pam resin, available from Applied Biosystems Inc., Foster City, Calif. on an Applied Biosystems Inc. 430A Peptide Synthesizer.

The t-butyloxycarbonyl (BOC) group is used as the N-amino protecting group during step-wise synthesis. Trifunctional amino acid side chains are protected with Ser (Bzl) and Thr(Bzl). Each residue is coupled twice, then capped with acetic anhydride before the next cycle of synthesis. Quantitative ninhydrin tests are performed at each cycle of the synthesis.

After removing the N-terminal Boc group in the usual fashion, biotin is attached by treating the peptide-resin in DMF with N-hydroxysuccinimide-biotin, available from Pierce Chemical Co. The biotin-peptide is cleaved from the resin by treatment with HF/anisole (10:1) for 1 hour at −20° to −5° C. The peptide resin is titrated with ether, the crude peptide dissolved in 50% acetic acid and the resin is removed by filtration. The filtrate is evaporated to dryness under reduced pressure and lyophilized from glacial acetic acid.

The crude peptide, in the dried lyophilized filtrate, is purified by preparative reverse phase chromatography on a Vydac C-18 column (250×22.5 mm) using a water/acetonitrile gradient, with each phase containing 0.1% TFA. Homogenous fractions, as determined by analytical HPLC, are pooled and the acetonitrile evaporated under reduced pressure; an aqueous solution of the pooled fractions is lyophilized. The purified peptide is characterized by time of flight mass spectroscopy which should give the anticipated (M+H)+.

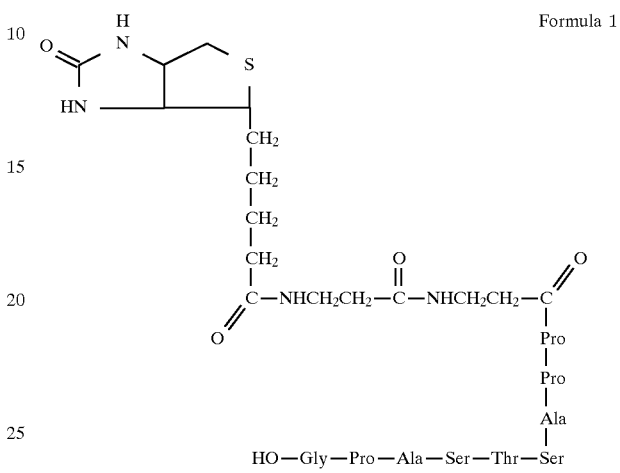

Formula 1 shows the peptide sequence, PPASTSAPG (SEQ. ID. NO.5), coupled to biotin.

There are numerous peptide sequences that are suitable for this assay. Some sequences are described in Elhammer et al. (1993) *J. Biol. Chem.*, 268, 10029–10038, incorporated by reference. Preferred sequences are nine amino acids in length although other lengths are also acceptable. A minimum of 3 amino acids can be recognized by the enzyme. Five amino acids or fewer are less efficient than more than five amino acids. Eight amino acids should perform well. Nine amino acids are preferred. The enzyme seems to recognize 4 amino acids on either side of the acceptor amino acid. Peptides containing ten, eleven, twelve or more amino acids should all function well.

The sequences in CHART I are taken from the Elhammer paper, id., all the peptide sequences in CHART I should work with the assay described herein. CHART I shows 196 glycosylated peptide segments. The glycosylated peptides are listed as enneapeptide (ennea, greek: nine) segments with the reactive Ser or Thr in the central position, designated as PO or as $R_5$. Accordingly, the amino acid side chains toward the $NH_2$ terminus are designated as the subsites $R_1$ to $R_4$ and those toward the COOH terminus as subsites $R_6$ to $R_9$, this is shown below.

(acceptor amino acids are Ser or Thr)

($NH_2$ terminus side) ▼ (COOH terminus side)

Nine residues is a preferred starting point, with the option that, depending on the results on the selectivity of the subsites, the peptide may be extended or truncated. The sequences in CHART I show that besides the obvious need for Ser or Thr in the PO (or $R_5$) position, no other subsite has an absolute requirement for any given amino acid.

The following amino acids are all suitable for positions $R_{1-4}$ and $R_{6-9}$: Asp, Asn, Glu, Gln, Ser, Gly, His, Arg, Thr, Ala, Pro, Tyr, Val, Met, Ile, Leu, Phe, Lys, Cys, Trp.

The enzyme is not highly specific, many sequences will work. Alternative amino acid sequences are also disclosed in the Elhammer paper, id. The acceptor amino acid is surrounded preferentially by Ser, Thr, Pro, Ala, and Gly residues, but in no specific order. Both serine and threonine are acceptor amino acids. An ideal glycosylation substrate could consist of the reactive residue surrounded on both sides by Ser, Thr, Pro, Ala, and Gly residues, without any specific order. The hydrogen bonding ability of the peptide backbone should probably remain intact, but the side chains could be varied within large limits without significant deleterious effects.

The amino acids Gly, Ala, Val, and Met are permitted to occur randomly. Perhaps more important is the fact that Asp, Asn, Arg, Tyr, Leu, Phe, Lys, Cys, and Trp occur only at very low frequencies and may decrease the probability of glycosylation.

The following acceptor peptides were synthesized: RTPPP (SEQ. ID. NO.3), RSPPP (SEQ. ID. NO.4), PPASTSAPG (SEQ. ID. NO.5), PPASSSAPG (SEQ. ID. NO.6), The preferred acceptor peptide is PPASTSAPG (SEQ. ID. NO.5). Note that the peptide RTPPP (SEQ. ID. NO.3) has a catalytic efficiency only half that of PPASTSAPG (SEQ. ID. NO.5). Further discussion of acceptor efficiencies can be found in Elhammer et al. (1993) *J. Biol. Chem.*, 268, 10029–10038.

The Streptavidin Coated SPA Beads

The limited capacity of the streptavidin coated SPA beads used, 115 pmol/mg, (average batch is 110–120 pmol/mg) necessitated the use of acceptor concentrations, in the assays, far below saturation.

The optimum acceptor concentration for assays employing 4 mg of the SPA beads, the maximal amount useable in 96-well plates, is shown in FIG. 1. Maximum incorporation of radioactivity, from the nucleotide sugar onto the acceptor peptide conjugate, occurs when the concentration of acceptor conjugate is approximately 17 $\mu$M. This maximum level of radioactivity incorporation indicates that low levels of enzyme activity are difficult to detect using this assay method. Comparatively high levels of enzyme activity are needed for positive detection. Typically we use 300 mU/assay. Note that other, more conventional assays can easily detect 1 mU of enzyme activity; however, other conventional assays cannot conveniently be used for screening purposes.

FIG. 1 shows the maximum on the incorporation curve (incorporation of radioactive GalNAc from the nucleotide sugar to the acceptor peptide conjugate) which probably reflects saturation of the SPA beads. One would expect a linear increase in radioactivity incorporation up to acceptor saturation if saturation of the SPA beads did not occur.

Figure 2:
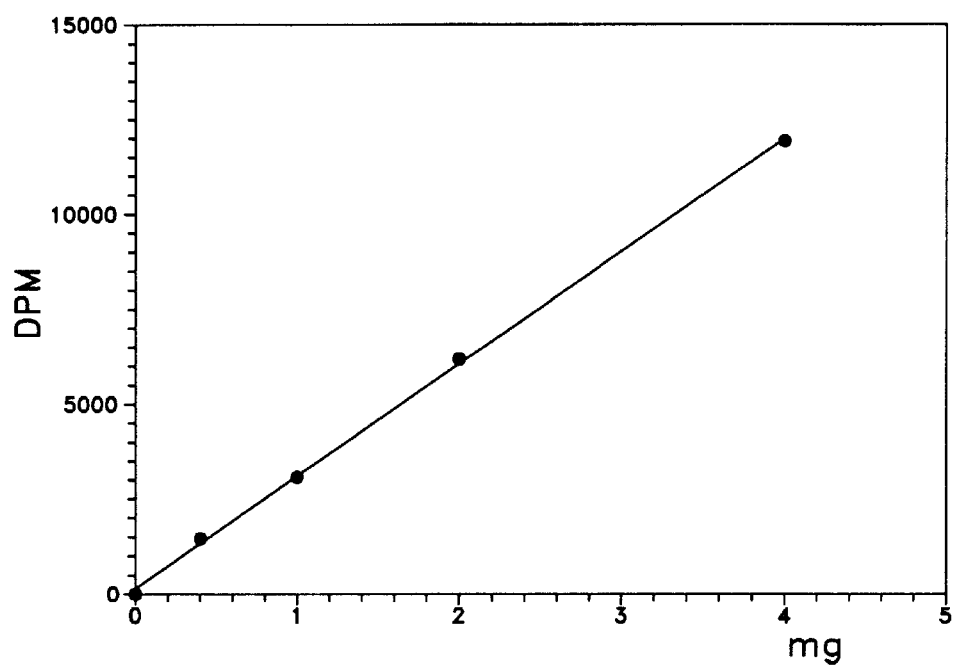
FIG. 2. Effect of SPA bead concentration on the recovery of radioactivity from the reaction product.

FIG. 2 shows the results when different amounts of SPA beads are added to the assay. FIG. 2 shows that lowering the amount of SPA beads in the assay results in a linear reduction in detected radioactivity, i.e. the amount of SPA beads added is clearly limiting the amount of radioactive product detectable by the assay. However, at 17 $\mu$M acceptor concentration and using 4 mg SPA beads, the assay shows a typical Michaelis-Menten type dependency of the limiting donor concentration.

Figure 3:
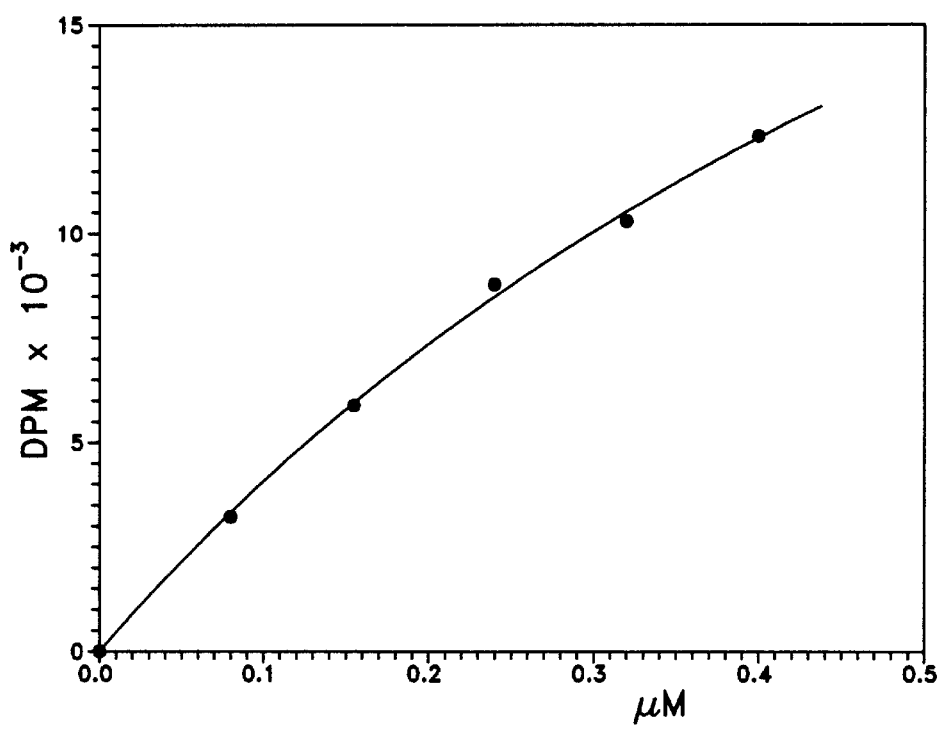
FIG. 3. Effect of UDP-GalNAc concentration on the formation of reaction product.

This typical Michaelis-Menten type dependency of the limiting donor concentration is shown in FIG. 3. In FIG. 3, the assay conditions are the same as those described for FIG. 1. The data in the table below (TABLE 1), taken from FIG. 3, indicateS the $K_m$ for UDP-GalNAc is calculated to be $K_m \approx 0.8$ $\mu$M.

Figure 4:
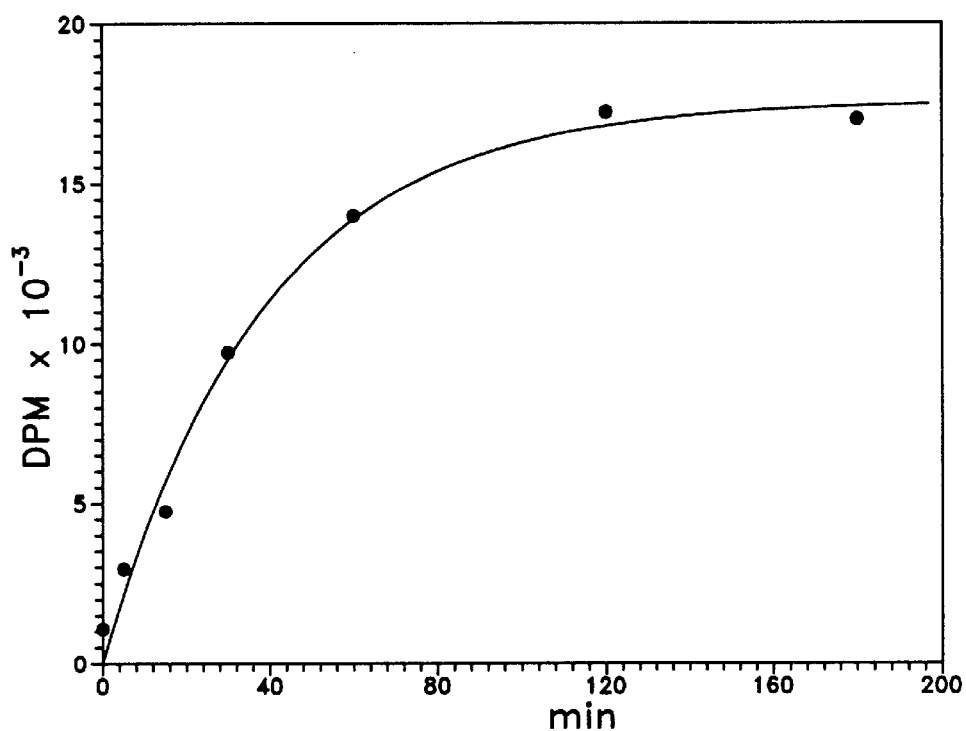
FIG. 4. Effect of incubation time on the formation of reaction product.

FIG. 4 shows time dependency, once again, typical integrated Michaelis-Menten type behavior is indicated by the largely linear shape of the product versus time curve for most of the duration of the reaction. Using the integrated form of the Michaelis-Menten equation and a nonlinear least squares fit method, we calculate $K_m$=0.38±0.12 $\mu$M for UDP-GalNAc under our experimental conditions. The agreement of the experimental data and the theoretical curve based on the best fit parameters of the Michaelis-Menten equation indicate that the reaction is uncomplicated by substrate inhibition or by enzyme decomposition. The slight curvature of the reaction during the first 60 minutes shows that the quantity of enzyme used in this assay is very probably an upper limit where linearity of the assay velocity versus enzyme concentration still obtains.

FIG. 4 shows the results of another aspect of this assay, the amount of enzyme used in the assay. The addition of increasing amounts of enzyme results in a linear increase in product formation up to approximately 600 mU. Our typical assay uses approximately 300 mU of enzyme.

Conventional assays for the evaluation of the biotinylated acceptor peptide were carried out in order to make comparisons with the SPA assay. These assays were carried out as described by Homa et al. (1994). A one cc Bond Elut column may be used for isolation of the reaction product. See, Homa, F. L., Baker, C. A., Thomsen, D. R., and Elhammer, Å.P. (1994) Prot. Expr. Purif in press., incorporated herein by reference. The SPA based assay is carried out on 96-well microtiter plates.

One ordinarily skilled in the art should be able to practice the invention without further instruction. The following examples are provided to further illustrate and not limit the invention. While the invention will now be described with reference to specific methods and embodiments, it will be appreciated that various modifications and changes, obvious to one skilled in the art, may be made without departing from the invention.

EXAMPLES

Example 1

A typical reaction. Reaction mixtures will vary depending on the specific experiment. See the figures and tables for the specific concentrations of various components. A typical reaction mixture contains the following components in a final volume of 40 $\mu$l: 2 $\mu$mol imidazole, pH 7.2, 0.4 $\mu$mol MnCl$_2$, 19.2 pmol (135,000 cpm) UDP-[$^3$H]-GalNAc, 0.7 nmol acceptor peptide (biotin-$\beta$A $\beta$A $\beta$A-PPASTSAPG (SEQ. ID. NO.8)) and approximately 300 mU of enzyme.

The reaction is incubated at 37° C. for 30 minutes, then the reaction is quenched by the addition of 10 $\mu$l 0.5M EDTA. One hundred microliters of a 40 mg/ml suspension of streptavidin SPA beads in PBS containing 20% glycerol is added to each reaction mixture (well on microtiter plate) and the plate is incubated at room temperature on an orbital shaker for 2 hours before the incorporated radioactivity is counted on a microplate scintillation counter.

Assays containing this peptide, in up to saturating concentrations, (and using reverse-phase columns for isolation of the reaction product) demonstrate that the $K_m$ for this acceptor is similar to the $K_m$ previously determined for the unbiotinylated peptide, 1.7 mM vs. 6.5 mM (Elhammer et al., 1993). Thus, the addition of biotin to the NH$_2$-terminus of PPASTSAPG (SEQ. ID. NO.5) does not adversely affect the efficiency of this acceptor. In fact, the slightly lower $K_m$ (vs. the unbiotinylated peptide) indicates that biotinylation may improve acceptor efficiency.

Example 2

FIG. 1. Effect of acceptor conjugate concentration on the formation of reaction product. Assays were carried out in a 96-well microtiter plate and contained 2 μmol imidazole, pH 7.2, 0.4 μmol $MnCl_2$, 19.2 pmol UDP-$^3$H-GalNAc, approximately 300 mU of enzyme and 0 to 30 μmol acceptor peptide, in a total volume of 40 μl. After incubation for 1 hour at 37°, the reaction was stopped by the addition of 10 μl of 0.5M EDTA. One hundred μl of a 40 mg/ml suspension of streptavidin SPA beads were added and, following incubation for two hours at room temperature, the radioactivity in the wells was counted in a Top Count scintillation counter. See FIG. 1 for results. The solid diagonal line, in FIG. 1, to the left of the vertical line, is a linear least squares fit of the data obtained when the acceptor peptide concentration was 13 μM and lower. The horizontal solid line was obtained by calculating the mean DPM when the acceptor peptide concentration was 17 μM and higher.

Example 3

FIG. 2. Effect of SPA bead concentration on the recovery of radioactivity from the reaction product. Assay conditions were as described for EXAMPLE 2. The acceptor conjugate concentration was 17 μM and the amount of SPA beads added to the assay was varied from 0 to 100 μl (4 mg). The solid line is a linear least squares fit to the data.

Example 4

FIG. 3. Effect of UDP-GalNAc concentration on the formation of reaction product. Assay conditions are the same as those described for EXAMPLE 2. The acceptor conjugate concentration was 17 μM. The amount of UDP-$^3$H-GalNAc varies from 0 to 28.8 pmol. The solid curve is a nonlinear least squares fit to the Michaelis-Menten equation where $V_{max}$=37.8±4.6×10$^3$ DPM/h and $K_m$=0.8±0.2 μM.

Example 5

FIG. 4. Effect of incubation time on the formation of reaction product. Assay conditions are the same as those described in EXAMPLE 2; acceptor conjugate concentration was 17 μM. The incubation time was varied from 0–8 hours. The solid curve is a nonlinear least squares fit to an integrated form of the Michaelis-Menten equation, where the $K_m$ for GalNAc was found to be 0.38±0.12 μM.

Example 6

Figure 5:
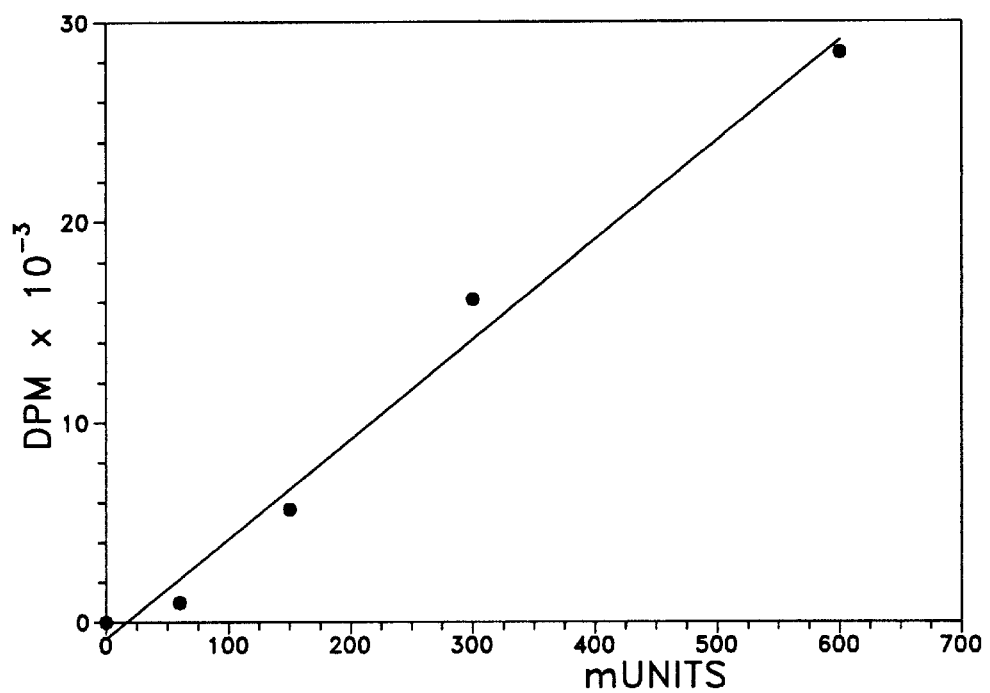
FIG. 5. Effect of enzyme concentration on the formation of reaction product.

FIG. 5. Effect of enzyme concentration on the formation of reaction product. Assay conditions are the same as those described in EXAMPLE 2. Acceptor conjugate concentration is 17 μM. The enzyme concentration in the assays was varied from 0–1500 mU. See, FIG. 5. The solid line is a linear least squares fit to the data.

CHART I follows. CHART I shows various amino acid substitutions for possible peptide sequences for the acceptor peptide. The chart show positions corresponding to positions $R_{1-4}$–(PO or $R_5$)–$R_{6-9}$. The $R_5$ (or PO) position is Ser or Thr.

CHART I

| | | | |
|---|---|---|---|
| PPTP—S—PSTP | TTSI—T—SDPK | PSFN—T—PSTR | GPVV—T—AQYE |
| TPPP—T—SGPT | ESPS—T—SEAL | ---S—T—GS-- | AVTG—S—EPGL |
| TPSP—S—TPPT | VAVP—T—TSA- | LVST—S—EPLS | DVNC—S—GPTP |
| VTPR—T—PPPS | TTTS—S—SVSK | ---S—T—TAVQ | SLGP—T—KETH |
| CPVP—S—TPPT | QTPT—S—GEPL | LPGV—T—GTSA | PLAG—T—SDLS |
| APAR—S—PSPS | VPGG—S—ATPQ | PEAT—T—ESII | ---Q—T—IATG |
| SPSP—S—TQPW | MHTT—T—IAEP | TTSS—S—VSKS | KSYI—S—SQTN |
| SGEP—T—STPT | GGTI—T—TNSP | TMHT—T—TIAE | ---L—S—TTEV |
| PATW—T—VPPP | PGLP—S—TGVS | GEQG—S—ATPG | DPGM—S—GWPD |
| APPP—S—LPSP | PVTI—T—NPAT | VTGT—S—AVTG | ISSQ—T—NDTH |
| NSAP—T—SSST | KPSA—T—SPGV | KMYT—T—SITS | HQIS—S—KLPT |
| MHTT—T—SSSV | ASAS—T—TMHT | ATPG—S—TTGR | THGL—S—ATIA |
| TPHA—T—SHPA | GGSA—T—PQQP | STGV—S—GLPG | VSEI—S—VRTV |
| SSVP—T—AQPQ | PSLP—S—PSRL | GLPS—T—GVSG | SDLS—T—ITSA |
| PAPA—T—EPTV | ATAA—T—AATA | AQPL—T—ENPR | QVLL—S—NPTS |
| -SKP—T—CPPP | TPSP—S—CCHP | LAKA—T—TAPA | ALSE—S—TTQL |
| PGMA—S—ASTT | -----T—ETPV | MLPF—T—PNSE | QGSA—T—PGNV |
| TVEP—T—PAPA | GVTG—T—SAVT | VPQE—T—PHAT | AHEV—S—EISV |
| AMHT—T—TSSS | TAPA—T—TRNT | TSDL—S—TITS | AWPL—S—LEPD |
| STIT—S—AATP | FTPN—S—ESPS | VTMA—T—GSLG | SEPL—S—SKMY |
| QTIA—T—GSPP | NPAT—S—SAVA | LPGP—S—DTPI | VSLE—T—SKGT |
| HTTT—S—SSVS | SEST—T—QLPG | ETPV—T—GEQG | NATV—T—AGKP |
| PPTP—S—PSCC | PVLP—T—QSAH | LPGS—T—---- | IIIP—T—INTI |
| ESII—T—STPE | WSTR—S—PNST | SSPL—S—TERM | ---R—S—AGAG |
| ELAP—T—APPE | AQAS—S—VPTA | MYTT—S—ITSD | FVHV—S—ESFP |
| TSAA—T—PTFT | PHAT—S—HPAV | GTSA—T—VSLE | --RS—S—VPGG |
| IITS—T—PETP | LPSP—S—RLPG | LATG—S—PPIA | DSQQ—T—AR-- |
| PLVS—T—SEPL | GPVP—T—PPDN | --LS—T—TEVA | AGAG—T—AGVD |
| --IA—T—PLPP | -PGG—S—SEPK | -STG—S—---- | AGFI—S—TEDP |
| PSPS—T—QPWE | --ST—T—AVQT | EQPL—T—ENPR | REYT—S—ARS- |
| VQTP—T—SGEP | AKAT—T—APAT | ISVR—T—VYPP | EPLS—S—KMYT |
| PGAL—S—ESTT | --MW—S—TRSP | LSTY—S—SIAT | VQKE—T—GVPE |
| LSTI—T—SAAT | TPTF—T—TEQD | TYAA—T—PRAH | EALS—T—YSSI |
| SESP—S—TSEA | VAMH—T—TTSS | SGVA—S—DPPV | NLPN—T—MTML |
| PNSE—S—PSTS | KAQA—S—SVPT | GLPG—S—T--- | IKNT—T—AVVQ |
| GTIT—T—NSPE | STYS—S—IATV | PDAA—S—AAPL | -RFS—S—AGIP |
| SAST—T—MHTT | TAVQ—T—PTSG | ATEP—T—VDSV | KADS—T—GDQT |
| AVPT—T—SA-- | STTV—S—LPHS | VSNA—T—VTAG | SKLP—T—QAGF |

CHART I

| | | | |
|---|---|---|---|
| SPST—S—EALS | DSVV—T—PEAT | PHQI—S—SKLP | AGVD—S—QQTA |
| GIPA—T—PGTS | PGST—T—GR-- | PNTM—T—MLPF | LFPK—S—SGVA |
| TSAV—T—GSEP | LSES—T—TQLP | --V.—T—LSPK | YQEV—S—IKMS |
| DSSS—S—KAPP | TPGS—T—TGR- | SKMY—T—TSIT | --RF—S—SAGI |
| TNPA—T—SSAV | APAT—T—RNTG | EVRP—T—SAVA | REDP—S—GTMY |
| MASA—S—TTMH | GLSA—T—IATS | -LST—T—EVAM | EEEG—S—GGGQ |
| PSAT—S—PGVM | LPPS—T—SINE | DNTV—T—SKPL | YYNQ—S—EAGS |
| SSIA—T—VPVT | MATG—S—LGPS | SEAL—S—TYSS | RFQD—S—SSSK |
| ARSP—S—PSTQ | GFIS—T—EDPS | SIKM—S—SVPQ | PENF—S—FPDD |
| PATS—S—AVAS | --R-—S—SVPG | -MWS—T—RSPN | GFNM—S—LLEN |
| EPLV—S—TSEP | TTMH—T—TTIA | GPVV—T—AQYE | NVYR—S—HLFF |

The sequences in this CHART are given SEQ. ID. numbers 10–205, in order, from top to bottom, left to right, that is, PPTP-S-PSTP is SEQ. ID. NO. 10, TPPP-T-SGPT is SEQ. ID. NO. 11, TPSP-S-TPPT is SEQ. ID. NO. 12, VTPR-T-PPPS is SEQ. ID. NO. 13, CPVP-S-TPPT is SEQ. ID. NO. 14, etc. The sequence numbers continue down the column to the bottom of the first column where EPLV-S-TSEP is SEQ. ID. NO. 58, then begin again at the top of the next column, TTSI-T-SDPK is SEQ. ID. NO. 59, ESPS-T-SEAL is SEQ. ID. NO. 60, etc.

We claim:

1. A rapid assay for measuring the activity of compounds that affect the activity of GalNAc-transferase comprising: mixing the following components in solution:
   a) GalNAc-transferase,
   b) said compounds, whose effect on GalNAc-transferase activity is to be measured,
   c) a biotin conjugated GalNAc-transferase acceptor peptide, where said acceptor peptide is comprised of the amino acids $R_1$ to $R_9$, as shown, $$R_1-R_2-R_3-R_4-R_5(\text{or PO})-R_6-R_7-R_8-R_9$$

where,
$R_5$ (or PO) is the acceptor amino acid and is selected from Ser or Thr;
$R_1$–$R_4$ are independent and are selected from Asp, Asn, Glu, Gln, Ser, Gly, His, Arg, Thr, Ala, Pro, Tyr, Val, Met, Ile, Leu, Phe, Lys, Cys, and Trp;
$R_6$–$R_9$ are independent and are selected from Asp, Asn, Glu, Gln, Ser, Gly, His, Arg, Thr, Ala, Pro, Tyr, Val, Met, Ile, Leu, Phe, Lys, Cys, and Trp;
   d) a radioactive nucleotide sugar,
   e) Scintillation Proximity Assay (SPA) beads, where said SPA beads are avidin or streptavidin coated, followed by measuring the radioactivity incorporated into said SPA beads.

2. An assay of claim 1, where, $R_1-R_4$ are independent and are selected from Ser, Gly, Thr, Ala, and Pro;

$R_6-R_9$ are independent and are selected from Ser, Gly, Thr, Ala, and Pro.

3. A rapid assay for measuring the activity of compounds that affect the activity of GalNAc-transferase comprising: mixing the following components in solution:

a) GalNAc-transferase, b) said compounds, whose effect on GalNAc-transferase activity is to be measured, c) a biotin conjugated GalNAc-transferase acceptor peptide, where said acceptor peptide is comprised of the amino acids $R_{-1}$ to $R_{11}$, as shown, $$R_{-1}-R_0-R_1-R_2-R_3-R_4-R_5(\text{or PO})-R_6-R_7-R_8-R_9-R_{10}-R_{11}$$

where, $R_5$ (or PO) is the acceptor amino acid and is selected from Ser or Thr;

$R_{-1}-R_4$ are independent and are selected from Asp, Asn, Glu, Gln, Ser, Gly, His, Arg, Thr, Ala, Pro, Tyr, Val, Met, Ile, Leu, Phe, Lys, Cys, and Trp;

$R_6-R_{11}$ are independent and are selected from Asp, Asn, Glu, Gln, Ser, Gly, His, Arg, Thr, Ala, Pro, Tyr, Val, Met, Ile, Leu, Phe, Lys, Cys, and Trp d) a radioactive nucleotide sugar, e) Scintillation Proximity Assay (SPA) beads, where said SPA beads are avidin or streptavidin coated, and measuring the radioactivity incorporated into said SPA beads.

4. An assay of claim 3 where $R_{-1}-R_4$ are independent and are selected from Ser, Gly, Thr, Ala, and Pro, $R_6-R_{11}$ are independent and are selected from Ser, Gly, Thr, Ala, and Pro.

5. A rapid assay for measuring the activity of compounds that affect the activity of GalNAc-transferase comprising: mixing the following components in aqueous solution:

a) GalNAc-transferase, b) said compounds, whose effect on GalNAc-transferase activity is to be measured, c) a biotin conjugated GalNAc-transferase acceptor peptide, where said acceptor peptide is comprised of a peptide having at least 3 amino acids where one of three amino acids is Ser or Thr, d) a radioactive nucleotide sugar, e) Scintillation Proximity Assay (SPA) beads, where said SPA beads are avidin or streptavidin coated, followed by measuring the radioactivity incorporated into said SPA beads.

6. An assay of claim 5 where components, a, b, c, and d are mixed before the addition of the SPA beads.

7. An assay of claim 5, where said acceptor peptide comprises the amino acids $R_{-1}$ to $R_{11}$, as shown, $$R_{-1}-R_0-R_1-R_2-R_3-R_4-R_5(\text{or PO})-R_6-R_7-R_8-R_9-R_{10}-R_{11}$$

where, $R_5$ (or PO) is the acceptor amino acid and is Ser or Thr;

$R_4$ and $R_6$ are independent and are Asp, Asn, Glu, Gln, Ser, Gly, His, Arg, Thr, Ala, Pro, Tyr, Val, Met, Ile, Leu, Phe, Lys, Cys, or Trp;

and $R_{-1}-R_3$ and $R_7-R_{11}$ are independent and are any of the following amino acids, Asp, Asn, Glu, Gln, Ser, Gly, His, Arg, Thr, Ala, Pro, Tyr, Val, Met, Ile, Leu, Phe, Lys, Cys, and Trp, or no amino acid at all.

8. An assay of claim 7 where said acceptor peptide comprises the amino acids $R_1$ to $R_9$, as shown, $$R_1-R_2-R_3-R_4-R_5(\text{or PO})-R_6-R_7-R_8-R_9$$

$R_5$ (or PO) is the acceptor amino acid and is Ser or Thr;

$R_4$ and $R_6$ are independent and are Asp, Asn, Glu, Gln, Ser, Gly, His, Arg, Thr, Ala, Pro, Tyr, Val, Met, Ile, Leu, Phe, Lys, Cys, or Trp;

and $R_1-R_3$ and $R_7-R_9$ are independent and are any of the following amino acids, Asp, Asn, Glu, Gln, Ser, Gly, His, Arg, Thr, Ala, Pro, Tyr, Val, Met, Ile, Leu, Phe, Lys, Cys, and Trp, or no amino acid at all.

9. An assay of claim 8 where said acceptor peptide comprises any of the sequences in CHART I, (i.e. SEQ. ID. NO.S 10–205).

10. An assay of claim 5 where said acceptor peptide is selected from the following peptides: RTPPP, (SEQ. ID. NO. 3) RSPPP (SEQ. ID. NO. 4), PPASTSAPG (SEQ. ID. NO. 5), and PPASSSAPG (SEQ. ID. NO. 6).

11. An assay of claim 5 where said acceptor peptide is selected from the following peptides: PPASTSAPG (SEQ. ID. NO. 5), and PPASSSAPG (SEQ. ID. NO. 6).

12. An assay of claim 11 where said acceptor peptide is PPASTSAPG (SEQ. ID. NO. 5).

13. An assay of claim 8 where said acceptor peptide has 9 amino acids in its sequence.

14. An assay of claim 13 where the 9 amino acids are selected from the following; Ser, Thr, Pro, Ala, and Gly.

* * * * *

SEQUENCE LISTING ( 1 ) GENERAL INFORMATION:

( i i i ) NUMBER OF SEQUENCES: 205

( 2 ) INFORMATION FOR SEQ ID NO:1:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
Ala  Glu  Glu  Gln  Lys  Leu  Ile  Ser  Glu  Glu  Asp  Leu  Leu  Arg  Lys  Arg
  1                  5                         10                            15
Arg  Glu  Gln  Leu  Lys  His  Lys  Leu  Glu  Gln  Leu  Arg  Asn  Ser  Cys
                20                        25                       30
```

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

```
Asp  Tyr  Lys  Asp  Asp  Asp  Lys
  1                  5
```

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:3:

Arg  Thr  Pro  Pro  Pro
      1                     5

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

Arg  Ser  Pro  Pro  Pro
      1                     5

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:5:

Pro  Pro  Ala  Ser  Thr  Ser  Ala  Pro  Gly
      1                     5

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:6:

Pro  Pro  Ala  Ser  Ser  Ser  Ala  Pro  Gly
            1                   5

( 2 ) INFORMATION FOR SEQ ID NO:7:

( i ) SEQUENCE CHARACTERISTICS:
                ( A ) LENGTH: 11 amino acids
                ( B ) TYPE: amino acid
                ( C ) STRANDEDNESS: single
                ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

Pro  Pro  Ala  Asp  Ser  Ser  Asp  Ser  Ala  Pro  Gly
            1                   5                        10

( 2 ) INFORMATION FOR SEQ ID NO:8:

( i ) SEQUENCE CHARACTERISTICS:
                ( A ) LENGTH: 12 amino acids
                ( B ) TYPE: amino acid
                ( C ) STRANDEDNESS: single
                ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:8:

Ala  Ala  Ala  Pro  Pro  Ala  Ser  Thr  Ser  Ala  Pro  Gly
            1                   5                        10

( 2 ) INFORMATION FOR SEQ ID NO:9:

( i ) SEQUENCE CHARACTERISTICS:
                ( A ) LENGTH: 11 amino acids
                ( B ) TYPE: amino acid
                ( C ) STRANDEDNESS: single
                ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:9:

Pro  Pro  Ala  Asp  Ser  Thr  Asp  Ser  Ala  Pro  Gly
            1                   5                        10

( 2 ) INFORMATION FOR SEQ ID NO:10:

( i ) SEQUENCE CHARACTERISTICS:
                ( A ) LENGTH: 9 amino acids
                ( B ) TYPE: amino acid
                ( C ) STRANDEDNESS: single (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:10:

```
Pro  Pro  Thr  Pro  Ser  Pro  Ser  Thr  Pro
1                   5
```

(2) INFORMATION FOR SEQ ID NO:11:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:11:

```
Thr  Pro  Pro  Pro  Thr  Ser  Gly  Pro  Thr
1                   5
```

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:12:

```
Thr  Pro  Ser  Pro  Ser  Thr  Pro  Pro  Thr
1                   5
```

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:13:

```
Val  Thr  Pro  Arg  Thr  Pro  Pro  Pro  Ser
1                   5
```

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:14:

Cys  Pro  Val  Pro  Ser  Thr  Pro  Pro  Thr
    1                         5

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:15:

Ala  Pro  Ala  Arg  Ser  Pro  Ser  Pro  Ser
    1                         5

( 2 ) INFORMATION FOR SEQ ID NO:16:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:16:

Ser  Pro  Ser  Pro  Ser  Thr  Gln  Pro  Trp
    1                         5

( 2 ) INFORMATION FOR SEQ ID NO:17:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:17:

Ser Gly Glu Pro Thr Ser Thr Pro Thr
    1               5

( 2 ) INFORMATION FOR SEQ ID NO:18:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:18:

Pro Ala Thr Trp Thr Val Pro Pro Pro
    1               5

( 2 ) INFORMATION FOR SEQ ID NO:19:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:19:

Ala Pro Pro Pro Ser Leu Pro Ser Pro
    1               5

( 2 ) INFORMATION FOR SEQ ID NO:20:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:20:

Asn Ser Ala Pro Thr Ser Ser Ser Thr
    1               5

( 2 ) INFORMATION FOR SEQ ID NO:21:

( i ) SEQUENCE CHARACTERISTICS:
      ( A ) LENGTH: 9 amino acids (B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:21:

```
Met His Thr Thr Thr Ser Ser Ser Val
1               5
```

(2) INFORMATION FOR SEQ ID NO:22:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:22:

```
Thr Pro His Ala Thr Ser His Pro Ala
1               5
```

(2) INFORMATION FOR SEQ ID NO:23:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:23:

```
Ser Ser Val Pro Thr Ala Gln Pro Gln
1               5
```

(2) INFORMATION FOR SEQ ID NO:24:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:24:

```
        Pro  Ala  Pro  Ala  Thr  Glu  Pro  Thr  Val
        1                   5
```

(2) INFORMATION FOR SEQ ID NO:25:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:25:

```
        Ser  Lys  Pro  Thr  Cys  Pro  Pro  Pro
        1                   5
```

(2) INFORMATION FOR SEQ ID NO:26:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:26:

```
        Pro  Gly  Met  Ala  Ser  Ala  Ser  Thr  Thr
        1                   5
```

(2) INFORMATION FOR SEQ ID NO:27:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:27:

```
        Thr  Val  Glu  Pro  Thr  Pro  Ala  Pro  Ala
        1                   5
```

(2) INFORMATION FOR SEQ ID NO:28:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:28:

```
Ala Met His Thr Thr Thr Ser Ser Ser
 1               5
```

(2) INFORMATION FOR SEQ ID NO:29:

(i) SEQUENCE CHARACTERISTICS:
        (A) LENGTH: 9 amino acids
        (B) TYPE: amino acid
        (C) STRANDEDNESS: single
        (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:29:

```
Ser Thr Ile Thr Ser Ala Ala Thr Pro
 1               5
```

(2) INFORMATION FOR SEQ ID NO:30:

(i) SEQUENCE CHARACTERISTICS:
        (A) LENGTH: 9 amino acids
        (B) TYPE: amino acid
        (C) STRANDEDNESS: single
        (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:30:

```
Gln Thr Ile Ala Thr Gly Ser Pro Pro
 1               5
```

(2) INFORMATION FOR SEQ ID NO:31:

(i) SEQUENCE CHARACTERISTICS:
        (A) LENGTH: 9 amino acids
        (B) TYPE: amino acid
        (C) STRANDEDNESS: single
        (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:31:

```
His Thr Thr Thr Ser Ser Ser Val Ser
 1               5
```

(2) INFORMATION FOR SEQ ID NO:32:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:32:

```
Pro  Pro  Thr  Pro  Ser  Pro  Ser  Cys  Cys
1                        5
```

( 2 ) INFORMATION FOR SEQ ID NO:33:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:33:

```
Glu  Ser  Ile  Ile  Thr  Ser  Thr  Pro  Glu
1                        5
```

( 2 ) INFORMATION FOR SEQ ID NO:34:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:34:

```
Glu  Leu  Ala  Pro  Thr  Ala  Pro  Pro  Glu
1                        5
```

( 2 ) INFORMATION FOR SEQ ID NO:35:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal (x i) SEQUENCE DESCRIPTION: SEQ ID NO:35:

Thr Ser Ala Ala Thr Pro Thr Phe Thr
1               5

(2) INFORMATION FOR SEQ ID NO:36:

(i) SEQUENCE CHARACTERISTICS:
       (A) LENGTH: 9 amino acids
       (B) TYPE: amino acid
       (C) STRANDEDNESS: single
       (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:36:

Ile Ile Thr Ser Thr Pro Glu Thr Pro
1               5

(2) INFORMATION FOR SEQ ID NO:37:

(i) SEQUENCE CHARACTERISTICS:
       (A) LENGTH: 9 amino acids
       (B) TYPE: amino acid
       (C) STRANDEDNESS: single
       (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:37:

Pro Leu Val Ser Thr Ser Glu Pro Leu
1               5

(2) INFORMATION FOR SEQ ID NO:38:

(i) SEQUENCE CHARACTERISTICS:
       (A) LENGTH: 7 amino acids
       (B) TYPE: amino acid
       (C) STRANDEDNESS: single
       (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:38:

Ile Ala Thr Pro Leu Pro Pro
1               5

(2) INFORMATION FOR SEQ ID NO:39:

(i) SEQUENCE CHARACTERISTICS:
       (A) LENGTH: 9 amino acids
       (B) TYPE: amino acid
       (C) STRANDEDNESS: single
       (D) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:39:

```
Pro  Ser  Pro  Ser  Thr  Gln  Pro  Trp  Glu
1                  5
```

( 2 ) INFORMATION FOR SEQ ID NO:40:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:40:

```
Val  Gln  Thr  Pro  Thr  Ser  Gly  Glu  Pro
1                  5
```

( 2 ) INFORMATION FOR SEQ ID NO:41:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:41:

```
Pro  Gly  Ala  Leu  Ser  Glu  Ser  Thr  Thr
1                  5
```

( 2 ) INFORMATION FOR SEQ ID NO:42:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:42:

```
Leu  Ser  Thr  Ile  Thr  Ser  Ala  Ala  Thr
1                  5
```

(2) INFORMATION FOR SEQ ID NO:43:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:43:

Ser Glu Ser Pro Ser Thr Ser Glu Ala
        1                  5

(2) INFORMATION FOR SEQ ID NO:44:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:44:

Pro Asn Ser Glu Ser Pro Ser Thr Ser
        1                  5

(2) INFORMATION FOR SEQ ID NO:45:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:45:

Gly Thr Ile Thr Thr Asn Ser Pro Glu
        1                  5

(2) INFORMATION FOR SEQ ID NO:46:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO ( v ) FRAGMENT TYPE: N-terminal ( x i ) SEQUENCE DESCRIPTION: SEQ ID NO:46:

```
Ser  Ala  Ser  Thr  Thr  Met  His  Thr  Thr
1                    5
```

( 2 ) INFORMATION FOR SEQ ID NO:47:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:47:

```
Ala  Val  Pro  Thr  Thr  Ser  Ala
1                    5
```

( 2 ) INFORMATION FOR SEQ ID NO:48:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:48:

```
Ser  Pro  Ser  Thr  Ser  Glu  Ala  Leu  Ser
1                    5
```

( 2 ) INFORMATION FOR SEQ ID NO:49:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:49:

```
Gly  Ile  Pro  Ala  Thr  Pro  Gly  Thr  Ser
1                    5
```

( 2 ) INFORMATION FOR SEQ ID NO:50:

( i ) SEQUENCE CHARACTERISTICS:
        ( A ) LENGTH: 9 amino acids
        ( B ) TYPE: amino acid
        ( C ) STRANDEDNESS: single (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:50:

```
Thr Ser Ala Val Thr Gly Ser Glu Pro
1               5
```

(2) INFORMATION FOR SEQ ID NO:51:

(i) SEQUENCE CHARACTERISTICS:
 (A) LENGTH: 9 amino acids
 (B) TYPE: amino acid
 (C) STRANDEDNESS: single
 (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:51:

```
Asp Ser Ser Ser Ser Lys Ala Pro Pro
1               5
```

(2) INFORMATION FOR SEQ ID NO:52:

(i) SEQUENCE CHARACTERISTICS:
 (A) LENGTH: 9 amino acids
 (B) TYPE: amino acid
 (C) STRANDEDNESS: single
 (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:52:

```
Thr Asn Pro Ala Thr Ser Ser Ala Val
1               5
```

(2) INFORMATION FOR SEQ ID NO:53:

(i) SEQUENCE CHARACTERISTICS:
 (A) LENGTH: 9 amino acids
 (B) TYPE: amino acid
 (C) STRANDEDNESS: single
 (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:53:

```
Met Ala Ser Ala Ser Thr Thr Met His
1               5
```

( 2 ) INFORMATION FOR SEQ ID NO:54:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:54:

Pro Ser Ala Thr Ser Pro Gly Val Met
        1                    5

( 2 ) INFORMATION FOR SEQ ID NO:55:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:55:

Ser Ser Ile Ala Thr Val Pro Val Thr
        1                    5

( 2 ) INFORMATION FOR SEQ ID NO:56:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:56:

Ala Arg Ser Pro Ser Pro Ser Thr Gln
        1                    5

( 2 ) INFORMATION FOR SEQ ID NO:57:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:57:

Pro Ala Thr Ser Ser Ala Val Ala Ser
1               5

( 2 ) INFORMATION FOR SEQ ID NO:58:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:58:

Glu Pro Leu Val Ser Thr Ser Glu Pro
1               5

( 2 ) INFORMATION FOR SEQ ID NO:59:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:59:

Thr Thr Ser Ile Thr Ser Asp Pro Lys
1               5

( 2 ) INFORMATION FOR SEQ ID NO:60:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:60:

Glu Ser Pro Ser Thr Ser Glu Ala Leu
1               5

( 2 ) INFORMATION FOR SEQ ID NO:61:

( i ) SEQUENCE CHARACTERISTICS:
    ( A ) LENGTH: 8 amino acids (B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:61:

Val Ala Val Pro Thr Thr Ser Ala
1               5

(2) INFORMATION FOR SEQ ID NO:62:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:62:

Thr Thr Thr Ser Ser Ser Val Ser Lys
1               5

(2) INFORMATION FOR SEQ ID NO:63:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:63:

Gln Thr Pro Thr Ser Gly Glu Pro Leu
1               5

(2) INFORMATION FOR SEQ ID NO:64:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:64:

```
         Val Pro Gly Gly Ser Ala Thr Pro Gln
         1               5
```

( 2 ) INFORMATION FOR SEQ ID NO:65:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:65:

```
         Met His Thr Thr Thr Ile Ala Glu Pro
         1               5
```

( 2 ) INFORMATION FOR SEQ ID NO:66:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:66:

```
         Gly Gly Thr Ile Thr Thr Asn Ser Pro
         1               5
```

( 2 ) INFORMATION FOR SEQ ID NO:67:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:67:

```
         Pro Gly Leu Pro Ser Thr Gly Val Ser
         1               5
```

( 2 ) INFORMATION FOR SEQ ID NO:68:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:68:

Pro Val Thr Ile Thr Asn Pro Ala Thr
1               5

(2) INFORMATION FOR SEQ ID NO:69:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:69:

Lys Pro Ser Ala Thr Ser Pro Gly Val
1               5

(2) INFORMATION FOR SEQ ID NO:70:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:70:

Ala Ser Ala Ser Thr Thr Met His Thr
1               5

(2) INFORMATION FOR SEQ ID NO:71:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:71:

Gly Gly Ser Ala Thr Pro Gln Gln Pro
1               5

(2) INFORMATION FOR SEQ ID NO:72:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:72:

```
Pro  Ser  Leu  Pro  Ser  Pro  Ser  Arg  Leu
1                   5
```

( 2 ) INFORMATION FOR SEQ ID NO:73:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:73:

```
Ala  Thr  Ala  Ala  Thr  Ala  Ala  Thr  Ala
1                   5
```

( 2 ) INFORMATION FOR SEQ ID NO:74:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:74:

```
Thr  Pro  Ser  Pro  Ser  Cys  Cys  His  Pro
1                   5
```

( 2 ) INFORMATION FOR SEQ ID NO:75:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:75:

Thr Glu Thr Pro Val
1               5

( 2 ) INFORMATION FOR SEQ ID NO:76:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:76:

Gly Val Thr Gly Thr Ser Ala Val Thr
1               5

( 2 ) INFORMATION FOR SEQ ID NO:77:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:77:

Thr Ala Pro Ala Thr Thr Arg Asn Thr
1               5

( 2 ) INFORMATION FOR SEQ ID NO:78:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:78:

Phe Thr Pro Asn Ser Glu Ser Pro Ser
1               5

( 2 ) INFORMATION FOR SEQ ID NO:79:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:79:

```
Asn  Pro  Ala  Thr  Ser  Ser  Ala  Val  Ala
1                  5
```

(2) INFORMATION FOR SEQ ID NO:80:

(i) SEQUENCE CHARACTERISTICS:
    (A) LENGTH: 9 amino acids
    (B) TYPE: amino acid
    (C) STRANDEDNESS: single
    (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:80:

```
Ser  Glu  Ser  Thr  Thr  Gln  Leu  Pro  Gly
1                  5
```

(2) INFORMATION FOR SEQ ID NO:81:

(i) SEQUENCE CHARACTERISTICS:
    (A) LENGTH: 9 amino acids
    (B) TYPE: amino acid
    (C) STRANDEDNESS: single
    (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:81:

```
Pro  Val  Leu  Pro  Thr  Gln  Ser  Ala  His
1                  5
```

(2) INFORMATION FOR SEQ ID NO:82:

(i) SEQUENCE CHARACTERISTICS:
    (A) LENGTH: 9 amino acids
    (B) TYPE: amino acid
    (C) STRANDEDNESS: single
    (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:82:

```
Trp  Ser  Thr  Arg  Ser  Pro  Asn  Ser  Thr
1                  5
```

( 2 ) INFORMATION FOR SEQ ID NO:83:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:83:

Ala Gln Ala Ser Ser Val Pro Thr Ala
    1                      5

( 2 ) INFORMATION FOR SEQ ID NO:84:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:84:

Pro His Ala Thr Ser His Pro Ala Val
    1                      5

( 2 ) INFORMATION FOR SEQ ID NO:85:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:85:

Leu Pro Ser Pro Ser Arg Leu Pro Gly
    1                      5

( 2 ) INFORMATION FOR SEQ ID NO:86:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:86:

```
Gly  Pro  Val  Pro  Thr  Pro  Pro  Asp  Asn
1                    5
```

( 2 ) INFORMATION FOR SEQ ID NO:87:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:87:

```
Pro  Gly  Gly  Ser  Ser  Glu  Pro  Lys
1                    5
```

( 2 ) INFORMATION FOR SEQ ID NO:88:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:88:

```
Ser  Thr  Thr  Ala  Val  Gln  Thr
1                    5
```

( 2 ) INFORMATION FOR SEQ ID NO:89:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:89:

```
Ala  Lys  Ala  Thr  Thr  Ala  Pro  Ala  Thr
1                    5
```

( 2 ) INFORMATION FOR SEQ ID NO:90:

( i ) SEQUENCE CHARACTERISTICS:
      ( A ) LENGTH: 7 amino acids
      ( B ) TYPE: amino acid
      ( C ) STRANDEDNESS: single ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:90:

```
Met  Trp  Ser  Thr  Arg  Ser  Pro
1                   5
```

( 2 ) INFORMATION FOR SEQ ID NO:91:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:91:

```
Thr  Pro  Thr  Phe  Thr  Thr  Glu  Gln  Asp
1                   5
```

( 2 ) INFORMATION FOR SEQ ID NO:92:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:92:

```
Val  Ala  Met  His  Thr  Thr  Thr  Ser  Ser
1                   5
```

( 2 ) INFORMATION FOR SEQ ID NO:93:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:93:

```
Lys  Ala  Gln  Ala  Ser  Ser  Val  Pro  Thr
1                   5
```

( 2 ) INFORMATION FOR SEQ ID NO:94:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:94:

Ser  Thr  Tyr  Ser  Ser  Ile  Ala  Thr  Val
        1                         5

( 2 ) INFORMATION FOR SEQ ID NO:95:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:95:

Thr  Ala  Val  Gln  Thr  Pro  Thr  Ser  Gly
        1                         5

( 2 ) INFORMATION FOR SEQ ID NO:96:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:96:

Ser  Thr  Thr  Val  Ser  Leu  Pro  His  Ser
        1                         5

( 2 ) INFORMATION FOR SEQ ID NO:97:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:97:

```
Asp Ser Val Val Thr Pro Glu Ala Thr
1               5
```

( 2 ) INFORMATION FOR SEQ ID NO:98:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:98:

```
Pro Gly Ser Thr Thr Gly Arg
1               5
```

( 2 ) INFORMATION FOR SEQ ID NO:99:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:99:

```
Leu Ser Glu Ser Thr Thr Gln Leu Pro
1               5
```

( 2 ) INFORMATION FOR SEQ ID NO:100:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:100:

```
Thr Pro Gly Ser Thr Thr Gly Arg
1               5
```

( 2 ) INFORMATION FOR SEQ ID NO:101:

( i ) SEQUENCE CHARACTERISTICS:
        ( A ) LENGTH: 9 amino acids (B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:101:

Ala Pro Ala Thr Thr Arg Asn Thr Gly
1               5

(2) INFORMATION FOR SEQ ID NO:102:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:102:

Gly Leu Ser Ala Thr Ile Ala Thr Ser
1               5

(2) INFORMATION FOR SEQ ID NO:103:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:103:

Leu Pro Pro Ser Thr Ser Ile Asn Glu
1               5

(2) INFORMATION FOR SEQ ID NO:104:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:104:

```
          Met  Ala  Thr  Gly  Ser  Leu  Gly  Pro  Ser
          1                   5
```

( 2 ) INFORMATION FOR SEQ ID NO:105:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:105:

```
          Gly  Phe  Ile  Ser  Thr  Glu  Asp  Pro  Ser
          1                   5
```

( 2 ) INFORMATION FOR SEQ ID NO:106:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:106:

```
          Arg  Ser  Ser  Val  Pro  Gly
          1                   5
```

( 2 ) INFORMATION FOR SEQ ID NO:107:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:107:

```
          Thr  Thr  Met  His  Thr  Thr  Thr  Ile  Ala
          1                   5
```

( 2 ) INFORMATION FOR SEQ ID NO:108:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:108:

Pro  Ser  Phe  Val  Thr  Pro  Ser  Thr  Arg
    1                       5

(2) INFORMATION FOR SEQ ID NO:109:

(i) SEQUENCE CHARACTERISTICS:
        (A) LENGTH: 4 amino acids
        (B) TYPE: amino acid
        (C) STRANDEDNESS: single
        (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:109:

Ser  Thr  Gly  Ser
    1

(2) INFORMATION FOR SEQ ID NO:110:

(i) SEQUENCE CHARACTERISTICS:
        (A) LENGTH: 9 amino acids
        (B) TYPE: amino acid
        (C) STRANDEDNESS: single
        (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:110:

Leu  Val  Ser  Thr  Ser  Glu  Pro  Leu  Ser
    1                       5

(2) INFORMATION FOR SEQ ID NO:111:

(i) SEQUENCE CHARACTERISTICS:
        (A) LENGTH: 6 amino acids
        (B) TYPE: amino acid
        (C) STRANDEDNESS: single
        (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:111:

Ser  Thr  Thr  Ala  Val  Gln
    1                   5

(2) INFORMATION FOR SEQ ID NO:112:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:112:

```
Leu  Pro  Gly  Val  Thr  Gly  Thr  Ser  Ala
1                   5
```

( 2 ) INFORMATION FOR SEQ ID NO:113:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:113:

```
Pro  Glu  Ala  Thr  Thr  Glu  Ser  Ile  Ile
1                   5
```

( 2 ) INFORMATION FOR SEQ ID NO:114:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:114:

```
Thr  Thr  Ser  Ser  Ser  Val  Ser  Lys  Ser
1                   5
```

( 2 ) INFORMATION FOR SEQ ID NO:115:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:115:

Thr Met His Thr Thr Thr Ile Ala Glu
1               5

( 2 ) INFORMATION FOR SEQ ID NO:116:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:116:

Gly Glu Gln Gly Ser Ala Thr Pro Gly
1               5

( 2 ) INFORMATION FOR SEQ ID NO:117:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:117:

Val Thr Gly Thr Ser Ala Val Thr Gly
1               5

( 2 ) INFORMATION FOR SEQ ID NO:118:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:118:

Lys Met Tyr Thr Thr Ser Ile Thr Ser
1               5

( 2 ) INFORMATION FOR SEQ ID NO:119:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:119:

```
Ala  Thr  Pro  Gly  Ser  Thr  Thr  Gly  Arg
1                   5
```

(2) INFORMATION FOR SEQ ID NO:120:

(i) SEQUENCE CHARACTERISTICS:
        (A) LENGTH: 9 amino acids
        (B) TYPE: amino acid
        (C) STRANDEDNESS: single
        (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:120:

```
Ser  Thr  Gly  Val  Ser  Gly  Leu  Pro  Gly
1                   5
```

(2) INFORMATION FOR SEQ ID NO:121:

(i) SEQUENCE CHARACTERISTICS:
        (A) LENGTH: 9 amino acids
        (B) TYPE: amino acid
        (C) STRANDEDNESS: single
        (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:121:

```
Gly  Leu  Pro  Ser  Thr  Gly  Val  Ser  Gly
1                   5
```

(2) INFORMATION FOR SEQ ID NO:122:

(i) SEQUENCE CHARACTERISTICS:
        (A) LENGTH: 9 amino acids
        (B) TYPE: amino acid
        (C) STRANDEDNESS: single
        (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:122:

```
Ala  Gln  Pro  Leu  Thr  Glu  Asn  Pro  Arg
1                   5
```

( 2 ) INFORMATION FOR SEQ ID NO:123:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:123:

Leu Ala Lys Ala Thr Thr Ala Pro Ala
        1                  5

( 2 ) INFORMATION FOR SEQ ID NO:124:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:124:

Met Leu Pro Phe Thr Pro Asn Ser Glu
        1                  5

( 2 ) INFORMATION FOR SEQ ID NO:125:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:125:

Val Pro Gln Glu Thr Pro His Ala Thr
        1                  5

( 2 ) INFORMATION FOR SEQ ID NO:126:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:126:

Thr Ser Asp Leu Ser Thr Ile Thr Ser
1               5

( 2 ) INFORMATION FOR SEQ ID NO:127:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:127:

Val Thr Met Ala Thr Gly Ser Leu Gly
1               5

( 2 ) INFORMATION FOR SEQ ID NO:128:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:128:

Leu Pro Gly Pro Ser Asp Thr Pro Ile
1               5

( 2 ) INFORMATION FOR SEQ ID NO:129:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:129:

Glu Thr Pro Val Thr Gly Glu Gln Gly
1               5

( 2 ) INFORMATION FOR SEQ ID NO:130:

( i ) SEQUENCE CHARACTERISTICS:
    ( A ) LENGTH: 5 amino acids
    ( B ) TYPE: amino acid
    ( C ) STRANDEDNESS: single (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:130:

Leu Pro Gly Ser Thr
1               5

(2) INFORMATION FOR SEQ ID NO:131:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:131:

Ser Ser Pro Leu Ser Thr Glu Arg Met
1               5

(2) INFORMATION FOR SEQ ID NO:132:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:132:

Met Tyr Thr Thr Ser Ile Thr Ser Asp
1               5

(2) INFORMATION FOR SEQ ID NO:133:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:133:

Gly Thr Ser Ala Thr Val Ser Leu Glu
1               5

( 2 ) INFORMATION FOR SEQ ID NO:134:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:134:

Leu Ala Thr Gly Ser Pro Pro Ile Ala
        1                 5

( 2 ) INFORMATION FOR SEQ ID NO:135:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:135:

Leu Ser Thr Thr Glu Val Ala
        1                5

( 2 ) INFORMATION FOR SEQ ID NO:136:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:136:

Ser Thr Gly Ser
        1

( 2 ) INFORMATION FOR SEQ ID NO:137:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO (i v) ANTI-SENSE: NO (v) FRAGMENT TYPE: N-terminal (x i) SEQUENCE DESCRIPTION: SEQ ID NO:137:

Glu Gln Pro Leu Thr Glu Asn Pro Arg
1               5

(2) INFORMATION FOR SEQ ID NO:138:

(i) SEQUENCE CHARACTERISTICS:
    (A) LENGTH: 9 amino acids
    (B) TYPE: amino acid
    (C) STRANDEDNESS: single
    (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:138:

Ile Ser Val Arg Thr Val Tyr Pro Pro
1               5

(2) INFORMATION FOR SEQ ID NO:139:

(i) SEQUENCE CHARACTERISTICS:
    (A) LENGTH: 9 amino acids
    (B) TYPE: amino acid
    (C) STRANDEDNESS: single
    (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:139:

Leu Ser Thr Tyr Ser Ser Ile Ala Thr
1               5

(2) INFORMATION FOR SEQ ID NO:140:

(i) SEQUENCE CHARACTERISTICS:
    (A) LENGTH: 9 amino acids
    (B) TYPE: amino acid
    (C) STRANDEDNESS: single
    (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:140:

Thr Tyr Ala Ala Thr Pro Arg Ala His
1               5

(2) INFORMATION FOR SEQ ID NO:141:

(i) SEQUENCE CHARACTERISTICS:
    (A) LENGTH: 9 amino acids (B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:141:

Ser Gly Val Ala Ser Asp Pro Pro Val
1               5

(2) INFORMATION FOR SEQ ID NO:142:

(i) SEQUENCE CHARACTERISTICS:
(A) LENGTH: 6 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:142:

Gly Leu Pro Gly Ser Thr
1               5

(2) INFORMATION FOR SEQ ID NO:143:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:143:

Pro Asp Ala Ala Ser Ala Ala Pro Leu
1               5

(2) INFORMATION FOR SEQ ID NO:144:

(i) SEQUENCE CHARACTERISTICS:
(A) LENGTH: 9 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:144:

Ala   Thr   Glu   Pro   Thr   Val   Asp   Ser   Val
            1                       5

( 2 ) INFORMATION FOR SEQ ID NO:145:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:145:

Val   Ser   Asn   Ala   Thr   Val   Thr   Ala   Gly
            1                       5

( 2 ) INFORMATION FOR SEQ ID NO:146:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:146:

Pro   His   Gln   Ile   Ser   Ser   Lys   Leu   Pro
            1                       5

( 2 ) INFORMATION FOR SEQ ID NO:147:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:147:

Pro   Asn   Thr   Met   Thr   Met   Leu   Pro   Phe
            1                       5

( 2 ) INFORMATION FOR SEQ ID NO:148:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:148:

Val Thr Leu Ser Pro Lys
1               5

( 2 ) INFORMATION FOR SEQ ID NO:149:

( i ) SEQUENCE CHARACTERISTICS:
( A ) LENGTH: 9 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:149:

Ser Lys Met Tyr Thr Thr Ser Ile Thr
1               5

( 2 ) INFORMATION FOR SEQ ID NO:150:

( i ) SEQUENCE CHARACTERISTICS:
( A ) LENGTH: 9 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:150:

Glu Val Arg Pro Thr Ser Ala Val Ala
1               5

( 2 ) INFORMATION FOR SEQ ID NO:151:

( i ) SEQUENCE CHARACTERISTICS:
( A ) LENGTH: 8 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:151:

Leu Ser Thr Thr Glu Val Ala Met
1               5

( 2 ) INFORMATION FOR SEQ ID NO:152:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:152:

Asp Asn Thr Val Thr Ser Lys Pro Leu
1               5

( 2 ) INFORMATION FOR SEQ ID NO:153:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:153:

Ser Glu Ala Leu Ser Thr Tyr Ser Ser
1               5

( 2 ) INFORMATION FOR SEQ ID NO:154:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:154:

Ser Ile Lys Met Ser Ser Val Pro Gln
1               5

( 2 ) INFORMATION FOR SEQ ID NO:155:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:155:

Met   Trp   Ser   Thr   Arg   Ser   Pro   Asn
    1                         5

( 2 ) INFORMATION FOR SEQ ID NO:156:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:156:

Gly   Pro   Val   Val   Thr   Ala   Gln   Tyr   Glu
    1                         5

( 2 ) INFORMATION FOR SEQ ID NO:157:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:157:

Gly   Pro   Val   Val   Thr   Ala   Gln   Tyr   Glu
    1                         5

( 2 ) INFORMATION FOR SEQ ID NO:158:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:158:

Ala   Val   Thr   Gly   Ser   Glu   Pro   Gly   Leu
    1                         5

( 2 ) INFORMATION FOR SEQ ID NO:159:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:159:

```
Asp Val Asn Cys Ser Gly Pro Thr Pro
1               5
```

( 2 ) INFORMATION FOR SEQ ID NO:160:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:160:

```
Ser Leu Gly Pro Ser Lys Glu Thr His
1               5
```

( 2 ) INFORMATION FOR SEQ ID NO:161:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:161:

```
Pro Ile Ala Gly Thr Ser Asp Leu Ser
1               5
```

( 2 ) INFORMATION FOR SEQ ID NO:162:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:162:

```
Gln Thr Ile Ala Thr Gly
1               5
```

( 2 ) INFORMATION FOR SEQ ID NO:163:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:163:

Lys  Ser  Tyr  Ile  Ser  Ser  Gln  Thr  Asn
    1                     5

( 2 ) INFORMATION FOR SEQ ID NO:164:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:164:

Leu  Ser  Thr  Thr  Glu  Val
    1                     5

( 2 ) INFORMATION FOR SEQ ID NO:165:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:165:

Asp  Pro  Gly  Met  Ser  Gly  Trp  Pro  Asp
    1                     5

( 2 ) INFORMATION FOR SEQ ID NO:166:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:166:

```
Ile  Ser  Ser  Gln  Thr  Asn  Asp  Thr  His
1                  5
```

( 2 ) INFORMATION FOR SEQ ID NO:167:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:167:

```
His  Gln  Ile  Ser  Ser  Lys  Leu  Pro  Thr
1                  5
```

( 2 ) INFORMATION FOR SEQ ID NO:168:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:168:

```
Thr  His  Gly  Leu  Ser  Ala  Thr  Ile  Ala
1                  5
```

( 2 ) INFORMATION FOR SEQ ID NO:169:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:169:

```
Val  Ser  Glu  Ile  Ser  Val  Arg  Thr  Val
1                  5
```

( 2 ) INFORMATION FOR SEQ ID NO:170:

( i ) SEQUENCE CHARACTERISTICS:
        ( A ) LENGTH: 9 amino acids
        ( B ) TYPE: amino acid
        ( C ) STRANDEDNESS: single ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:170:

Ser Asp Leu Ser Thr Ile Thr Ser Ala
1               5

( 2 ) INFORMATION FOR SEQ ID NO:171:

( i ) SEQUENCE CHARACTERISTICS:
( A ) LENGTH: 9 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:171:

Gln Val Leu Leu Ser Asn Pro Thr Ser
1               5

( 2 ) INFORMATION FOR SEQ ID NO:172:

( i ) SEQUENCE CHARACTERISTICS:
( A ) LENGTH: 9 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:172:

Ala Leu Ser Glu Ser Thr Thr Gln Leu
1               5

( 2 ) INFORMATION FOR SEQ ID NO:173:

( i ) SEQUENCE CHARACTERISTICS:
( A ) LENGTH: 9 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:173:

Gln Gly Ser Ala Thr Pro Gly Asn Val
1               5

( 2 ) INFORMATION FOR SEQ ID NO:174:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:174:

Ala His Glu Val Ser Glu Ile Ser Val
    1          5

( 2 ) INFORMATION FOR SEQ ID NO:175:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:175:

Ala Trp Pro Leu Ser Leu Glu Pro Asp
    1          5

( 2 ) INFORMATION FOR SEQ ID NO:176:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:176:

Ser Glu Pro Leu Ser Ser Lys Met Tyr
    1          5

( 2 ) INFORMATION FOR SEQ ID NO:177:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:177:

```
Val Ser Leu Glu Thr Ser Lys Gly Thr
1               5
```

( 2 ) INFORMATION FOR SEQ ID NO:178:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:178:

```
Asn Ala Thr Val Thr Ala Gly Lys Pro
1               5
```

( 2 ) INFORMATION FOR SEQ ID NO:179:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:179:

```
Ile Ile Ile Pro Thr Ile Asn Thr Ile
1               5
```

( 2 ) INFORMATION FOR SEQ ID NO:180:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:180:

```
Arg Ser Ala Gly Ala Gly
1               5
```

( 2 ) INFORMATION FOR SEQ ID NO:181:

( i ) SEQUENCE CHARACTERISTICS:
        ( A ) LENGTH: 9 amino acids (B) TYPE: amino acid
              (C) STRANDEDNESS: single
              (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:181:

Phe  Val  His  Val  Ser  Glu  Ser  Phe  Pro
              1                   5

(2) INFORMATION FOR SEQ ID NO:182:

(i) SEQUENCE CHARACTERISTICS:
              (A) LENGTH: 7 amino acids
              (B) TYPE: amino acid
              (C) STRANDEDNESS: single
              (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:182:

Arg  Ser  Ser  Val  Pro  Gly  Gly
              1                   5

(2) INFORMATION FOR SEQ ID NO:183:

(i) SEQUENCE CHARACTERISTICS:
              (A) LENGTH: 7 amino acids
              (B) TYPE: amino acid
              (C) STRANDEDNESS: single
              (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:183:

Asp  Ser  Gln  Gln  Thr  Ala  Arg
              1                   5

(2) INFORMATION FOR SEQ ID NO:184:

(i) SEQUENCE CHARACTERISTICS:
              (A) LENGTH: 9 amino acids
              (B) TYPE: amino acid
              (C) STRANDEDNESS: single
              (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:184:

Ala Gly Ala Gly Thr Ala Gly Val Asp
1               5

(2) INFORMATION FOR SEQ ID NO:185:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:185:

Ala Gly Phe Ile Ser Thr Glu Asp Pro
1               5

(2) INFORMATION FOR SEQ ID NO:186:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:186:

Arg Glu Tyr Thr Ser Ala Arg Ser
1               5

(2) INFORMATION FOR SEQ ID NO:187:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:187:

Glu Pro Leu Ser Ser Lys Met Tyr Thr
1               5

(2) INFORMATION FOR SEQ ID NO:188:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:188:

Val Gln Lys Glu Thr Gly Val Pro Glu
1               5

(2) INFORMATION FOR SEQ ID NO:189:

(i) SEQUENCE CHARACTERISTICS:
 (A) LENGTH: 9 amino acids
 (B) TYPE: amino acid
 (C) STRANDEDNESS: single
 (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:189:

Glu Ala Leu Ser Thr Tyr Ser Ser Ile
1               5

(2) INFORMATION FOR SEQ ID NO:190:

(i) SEQUENCE CHARACTERISTICS:
 (A) LENGTH: 9 amino acids
 (B) TYPE: amino acid
 (C) STRANDEDNESS: single
 (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:190:

Asn Leu Pro Asn Thr Met Thr Met Leu
1               5

(2) INFORMATION FOR SEQ ID NO:191:

(i) SEQUENCE CHARACTERISTICS:
 (A) LENGTH: 9 amino acids
 (B) TYPE: amino acid
 (C) STRANDEDNESS: single
 (D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:191:

Ile Lys Asn Thr Thr Ala Val Val Gln
1               5

(2) INFORMATION FOR SEQ ID NO:192:

(i) SEQUENCE CHARACTERISTICS:
    (A) LENGTH: 8 amino acids
    (B) TYPE: amino acid
    (C) STRANDEDNESS: single
    (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:192:

Arg Phe Ser Ser Ala Gly Ile Pro
    1               5

(2) INFORMATION FOR SEQ ID NO:193:

(i) SEQUENCE CHARACTERISTICS:
    (A) LENGTH: 9 amino acids
    (B) TYPE: amino acid
    (C) STRANDEDNESS: single
    (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:193:

Lys Ala Asp Ser Thr Gly Asp Gln Thr
    1               5

(2) INFORMATION FOR SEQ ID NO:194:

(i) SEQUENCE CHARACTERISTICS:
    (A) LENGTH: 9 amino acids
    (B) TYPE: amino acid
    (C) STRANDEDNESS: single
    (D) TOPOLOGY: unknown (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:194:

Ser Lys Leu Pro Thr Gln Ala Gly Phe
    1               5

(2) INFORMATION FOR SEQ ID NO:195:

(i) SEQUENCE CHARACTERISTICS:
    (A) LENGTH: 9 amino acids
    (B) TYPE: amino acid
    (C) STRANDEDNESS: single
    (D) TOPOLOGY: unknown (ii) MOLECULE TYPE: peptide (iii) HYPOTHETICAL: NO (iv) ANTI-SENSE: NO (v) FRAGMENT TYPE: N-terminal ( x i ) SEQUENCE DESCRIPTION: SEQ ID NO:195:

Ala Gly Val Asp Ser Gln Gln Thr Ala
1               5

( 2 ) INFORMATION FOR SEQ ID NO:196:

( i ) SEQUENCE CHARACTERISTICS:
( A ) LENGTH: 9 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:196:

Leu Phe Pro Lys Ser Ser Gly Val Ala
1               5

( 2 ) INFORMATION FOR SEQ ID NO:197:

( i ) SEQUENCE CHARACTERISTICS:
( A ) LENGTH: 9 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:197:

Tyr Gln Glu Val Ser Ile Lys Met Ser
1               5

( 2 ) INFORMATION FOR SEQ ID NO:198:

( i ) SEQUENCE CHARACTERISTICS:
( A ) LENGTH: 7 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:198:

Arg Phe Ser Ser Ala Gly Ile
1               5

( 2 ) INFORMATION FOR SEQ ID NO:199:

( i ) SEQUENCE CHARACTERISTICS:
( A ) LENGTH: 9 amino acids
( B ) TYPE: amino acid
( C ) STRANDEDNESS: single
( D ) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:199:

```
Arg Glu Asp Pro Ser Gly Thr Met Tyr
1               5
```

(2) INFORMATION FOR SEQ ID NO:200:

(i) SEQUENCE CHARACTERISTICS:
(A) LENGTH: 9 amino acids
(B) TYPE: amino acid
(C) STRANDEDNESS: single
(D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:200:

```
Glu Glu Glu Gly Ser Gly Gly Gly Gln
1               5
```

(2) INFORMATION FOR SEQ ID NO:201:

(i) SEQUENCE CHARACTERISTICS:
(A) LENGTH: 9 amino acids
(B) TYPE: amino acid
(C) STRANDEDNESS: single
(D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:201:

```
Tyr Tyr Asn Gln Ser Glu Ala Gly Ser
1               5
```

(2) INFORMATION FOR SEQ ID NO:202:

(i) SEQUENCE CHARACTERISTICS:
(A) LENGTH: 9 amino acids
(B) TYPE: amino acid
(C) STRANDEDNESS: single
(D) TOPOLOGY: unknown (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:202:

```
Arg Phe Gln Asp Ser Ser Ser Ser Lys
1               5
```

( 2 ) INFORMATION FOR SEQ ID NO:203:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:203:

Pro  Glu  Asn  Phe  Ser  Phe  Pro  Asp  Asp
      1                           5

( 2 ) INFORMATION FOR SEQ ID NO:204:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:204:

Gly  Phe  Asn  Met  Ser  Leu  Leu  Glu  Asn
      1                           5

( 2 ) INFORMATION FOR SEQ ID NO:205:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:205:

Asn  Val  Tyr  Arg  Ser  His  Leu  Phe  Phe
      1                           5